US009827427B2

(12) United States Patent
Saha et al.

(10) Patent No.: US 9,827,427 B2
(45) Date of Patent: *Nov. 28, 2017

(54) USER INTERFACE SYSTEM FOR USE WITH MULTIPOLAR PACING LEADS

(71) Applicant: CARDIAC PACEMAKERS, INC., St. Paul, MN (US)

(72) Inventors: Sunipa Saha, Shoreview, MN (US); Kenneth N. Hayes, Osakis, MN (US); Keith L. Herrmann, Minneapolis, MN (US); James R. Kalgren, Lino Lakes, MN (US); Aaron R. McCabe, Edina, MN (US); Holly Elizabeth Rockweiler, San Francisco, CA (US); Shibaji Shome, Arden Hills, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/858,769

(22) Filed: Sep. 18, 2015

(65) Prior Publication Data

US 2016/0008610 A1 Jan. 14, 2016

Related U.S. Application Data

(63) Continuation of application No. 13/198,499, filed on Aug. 4, 2011, now Pat. No. 9,138,585.
(Continued)

(51) Int. Cl.
*A61N 1/00* (2006.01)
*A61N 1/372* (2006.01)
(Continued)

(52) U.S. Cl.
CPC ......... *A61N 1/37247* (2013.01); *A61N 1/056* (2013.01); *A61N 1/3686* (2013.01); *A61N 1/37241* (2013.01); *A61N 1/36185* (2013.01)

(58) Field of Classification Search
CPC .. A61N 1/056; A61N 1/3686; A61N 1/36185; A61N 1/37241; A61N 1/37247
See application file for complete search history.

(56) References Cited

U.S. PATENT DOCUMENTS

| | | |
|---|---|---|
| 3,757,792 A | 9/1973 | Mulier et al. |
| 4,106,512 A | 8/1978 | Bisping et al. |

(Continued)

FOREIGN PATENT DOCUMENTS

| | | |
|---|---|---|
| EP | 1184050 | 3/2002 |
| EP | 1578490 | 9/2005 |

(Continued)

OTHER PUBLICATIONS

Boston Scientific, "Cardiac Resynchronization Therapy High Energy Defibrillator," Cognis 100-D System Guide, Boston Scientific (Jan. 1, 2008), 458 pages.

(Continued)

*Primary Examiner* — Mallika D Fairchild
(74) *Attorney, Agent, or Firm* — Pauly, DeVries Smith & Deffner LLC

(57) ABSTRACT

An interactive representation of electrostimulation electrodes or vectors can be provided, such as for configuring combinations of electrostimulation electrodes. In an example, electrodes or test parameters can be presented graphically or in a table. A user interface can be configured to receive user-input designating electrode combinations or vectors for test or for use in programming an implantable or ambulatory medical device. The interface can be used to indicate suggested electrode combinations or vectors in (Continued)

response to a first selection of an electrode. Tests can be performed on electrode combinations and vectors, and the results of the tests can be presented to a user using the interactive representation. In an example, test results can be analyzed by a processor and optionally used to program an implantable or ambulatory medical device.

18 Claims, 14 Drawing Sheets

Related U.S. Application Data

(60) Provisional application No. 61/371,369, filed on Aug. 6, 2010.

(51) Int. Cl.
*A61N 1/368* (2006.01)
*A61N 1/05* (2006.01)
*A61N 1/36* (2006.01)

(56) References Cited

U.S. PATENT DOCUMENTS

| | | | |
|---|---|---|---|
| 4,217,913 A | 8/1980 | Dutcher et al. | |
| 4,628,934 A | 12/1986 | Pohndorf et al. | |
| 4,711,251 A | 12/1987 | Stokes et al. | |
| 4,922,607 A | 5/1990 | Upton et al. | |
| 5,117,824 A | 6/1992 | Keimel et al. | |
| 5,246,014 A | 9/1993 | Williams et al. | |
| 5,317,633 A | 5/1994 | Hiraiwa | |
| 5,324,310 A | 6/1994 | Greeninger et al. | |
| 5,534,018 A | 7/1996 | Wahlstrand et al. | |
| 5,584,873 A | 12/1996 | Shoberg et al. | |
| 5,601,615 A | 2/1997 | Markowitz et al. | |
| 5,713,937 A * | 2/1998 | Nappholz | A61N 1/37247 607/27 |
| 5,861,012 A | 1/1999 | Stroebel | |
| 5,891,179 A | 4/1999 | Er et al. | |
| 5,916,163 A | 6/1999 | Panescu et al. | |
| 5,987,746 A | 11/1999 | Williams et al. | |
| 6,014,581 A | 1/2000 | Whayne et al. | |
| 6,052,624 A * | 4/2000 | Mann | A61N 1/37247 607/46 |
| 6,493,586 B1 | 12/2002 | Stahmann et al. | |
| 6,772,008 B2 | 8/2004 | Zhu et al. | |
| 6,782,291 B1 | 8/2004 | Bornzin et al. | |
| 6,978,178 B2 | 12/2005 | Sommer et al. | |
| 7,123,963 B2 | 10/2006 | Sawchuk et al. | |
| 7,236,826 B2 | 6/2007 | Wentkowski et al. | |
| 7,299,093 B2 | 11/2007 | Zhu et al. | |
| 7,383,091 B1 | 6/2008 | Chitre et al. | |
| 7,647,108 B2 | 1/2010 | Freeberg et al. | |
| 7,792,585 B1 | 9/2010 | Shelchuk et al. | |
| 8,615,297 B2 | 12/2013 | Brooke et al. | |
| 8,983,602 B2 | 3/2015 | Brooke et al. | |
| 9,008,775 B2 | 4/2015 | Brooke et al. | |
| 9,037,239 B2 | 5/2015 | Brooke et al. | |
| 9,138,585 B2 | 9/2015 | Saha et al. | |
| 2002/0077669 A1 | 6/2002 | Lindh et al. | |
| 2005/0149138 A1* | 7/2005 | Min | A61B 5/04012 607/27 |
| 2006/0259099 A1 | 11/2006 | Goetz et al. | |
| 2008/0294215 A1 | 11/2008 | Sathaye et al. | |
| 2008/0300644 A1 | 12/2008 | Sathaye et al. | |
| 2009/0018632 A1 | 1/2009 | Zdeblick et al. | |
| 2009/0043351 A1 | 2/2009 | Sathaye et al. | |
| 2009/0287271 A1* | 11/2009 | Blum | A61N 1/37247 607/45 |
| 2010/0010566 A1 | 1/2010 | Thacker et al. | |
| 2012/0035685 A1 | 2/2012 | Saha et al. | |
| 2013/0268018 A1 | 10/2013 | Brooke et al. | |
| 2013/0296961 A1 | 11/2013 | Brooke et al. | |
| 2014/0005741 A1 | 1/2014 | Brooke et al. | |
| 2014/0074177 A1 | 3/2014 | Sathaye et al. | |
| 2014/0194942 A1 | 7/2014 | Sathaye et al. | |
| 2015/0190639 A1 | 7/2015 | Sathaye et al. | |

FOREIGN PATENT DOCUMENTS

| | | |
|---|---|---|
| EP | 2600936 | 6/2013 |
| WO | 0174441 | 10/2001 |
| WO | 03092807 | 11/2003 |
| WO | 2012019036 | 2/2012 |

OTHER PUBLICATIONS

Boston Scientific, "Display Image: Lead Configuration Settings, Cognis 100-D Software Application," Cognis/Teligen Operating Screen Image, (Jan. 1, 2008), 1 page.

Boston Scientific, "Display Image: Lead Testing, Cognis 100-D Software Application," Cognis/Teligen Operating Screen Image, (Jan. 1, 2008), 1 page.

"Communication Pursuant to Rules 161(1) and 162 EPC," for European Patent Application No. 11743748.3, dated Mar. 13, 2013 (2 pages).

"File History," for U.S. Appl. No. 13/198,499, from Aug. 4, 2011 to Sep. 3, 2015 (391 pages).

"International Preliminary Report on Patentability," for PCT/US2011/046637, dated Feb. 21, 2013, 7 pages.

"Notice of Allowance," for U.S. Appl. No. 13/198,499, dated Jun. 8, 2015 (7 pages).

"Response to Rules 161(1) and 162 EPC," for European Patent Application No. 11743748.3, dated Mar. 13, 2013 and filed with the EPO Sep. 18, 2013 (17 pages).

"Search Report," for PCT/US2011/046637, dated Nov. 9, 2011 (4 pages).

"Written Opinion," for PCT/US2011/046637, dated Nov. 9, 2011 (5 pages).

"Communication Pursuant to Article 94(3) EPC," for European Patent Application No. 11743748.3 dated Jan. 30, 2017 (3 pages).

\* cited by examiner

A○◄────○B    A○────►○B
FIG. 2B      FIG. 2C
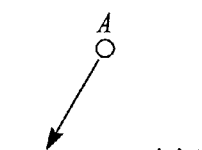
FIG. 2D
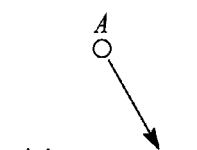
FIG. 2E
FIG. 2F
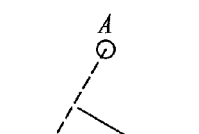
FIG. 2G
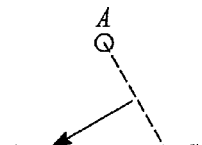
FIG. 2H
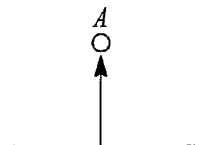
FIG. 2I
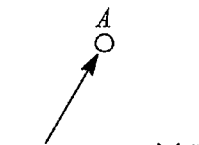
FIG. 2J
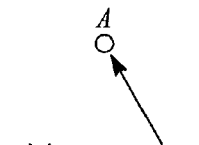
FIG. 2K
FIG. 2L
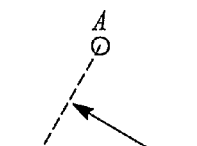
FIG. 2M
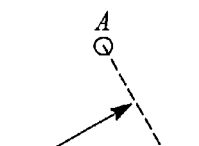
FIG. 2N
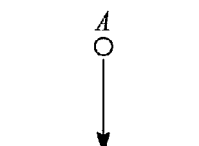
FIG. 2O

USER INTERFACE SYSTEM FOR USE WITH MULTIPOLAR PACING LEADS

CROSS REFERENCE TO RELATED APPLICATIONS

This application is a continuation application of U.S. application Ser. No. 13/198,499, filed Aug. 4, 2011, which claims the benefit of U.S. Provisional Application No. 61/371,369, filed Aug. 6, 2010, the contents of which are herein incorporated by reference in their entireties.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software, user interface screen representations, and data as described below and in the drawings that form a part of this document: Copyright 2010, Cardiac Pacemakers, Inc., All Rights Reserved.

BACKGROUND

Cardiac rhythm management devices can include implantable or ambulatory devices, such as pacemakers, cardioverter defibrillators, or devices that can monitor one or more physiological parameters, or provide one or a combination of pacing, defibrillation, or cardiac resynchronization therapies. In an example, such devices can be configured for use with a plurality of implanted or external electrodes, such as to detect or treat cardiac conditions. Selecting a proper electrode combination, or vector, for sensing or pacing can help ensure effective treatment. Sommer et al., in U.S. Pat. No. 6,978,178, entitled METHOD AND APPARATUS FOR SELECTING AN OPTIMAL ELECTRODE CONFIGURATION OF A MEDICAL ELECTRICAL LEAD HAVING A MULTIPLE ELECTRODE ARRAY, refers to a microprocessor performing a threshold search corresponding to combinations of electrodes to determine an optimal pacing threshold, and a microprocessor selecting electrodes corresponding to the optimal threshold. (See Sommer et al. at col. 4, 1. 27-32.) Lindh et al., in U.S. Pat. No. 7,236,826, entitled SYSTEM AND METHOD FOR GRAPHICALLY CONFIGURING LEADS, refers to graphically representing a medical device configuration on a user display. (See Lindh et al. at Abstract.)

OVERVIEW

Implantable or ambulatory medical devices configured to deliver electrical energy or to sense physiological events are in widespread use. The sophistication of such devices has evolved over time to incorporate functions that improve device efficiency and efficacy. One such improvement is the integration of multiple electrode leads with implantable or ambulatory medical devices. An implantable lead including multiple electrodes can provide an increased number of pacing or sensing configurations such that, when used properly, an implantable or ambulatory device can more effectively deliver therapy or monitor patient heart signals.

In an example, a pacing configuration can include an implantable medical device, an electronics assembly, and an electrode. The electronics assembly can be contained within a conductive housing of the implantable device, and the electrode can be contained within an implantable lead. The electrode can be electrically coupled to the electronics assembly and the implantable device. In an example, a distal portion of the implantable lead can be configured to be affixed to or placed against a heart wall. To achieve pacing, a pacing pulse can be delivered between the electrode and the conductive housing of the implantable medical device, establishing a unipolar pacing vector. A bipolar pacing vector can be established by providing two nearby electrodes (for example, on a single implantable lead) and delivering a pacing pulse from one electrode to the other. In both unipolar and bipolar pacing arrangements, the effectiveness of the pacing pulse can be affected by the location of the implanted electrodes.

Over time, as a host subject moves about and carries on with normal day-to-day activities, an implantable lead can shift or become dislodged. Such movement of an implantable lead can cause electrodes associated with that lead to move, and can affect pacing or sensing efficacy. For example, an electrode in a new location may not properly stimulate cardiac tissue. To address this problem, a lead can include an active fixation device, such as a helical coil at its distal tip.

Active fixation is not required. Passive fixation can involve positioning the electrode to be pressed against cardiac tissue, such as by providing a desired bend or other lead shape that can be used to push the electrode against cardiac tissue. Or, an implantable lead can include multiple electrodes. For example, multiple electrodes can be located as desired along all or a designated portion of the length of an implantable lead, such as between its proximal and distal ends. This can include two nearby electrodes, such as for bipolar pacing. The multiple electrodes can be individually addressable by an implantable medical device, and an implantable medical device can be configured to sense lead location changes and adapt electrode usage accordingly.

As the number of implanted electrodes increases, the clinician is confronted with the challenge of appropriately selecting pacing and sensing vectors. A carefully chosen vector can improve pacing or sensing efficacy. This, in turn, can improve the useful life of an implanted device. This document describes, among other things, an apparatus and method for quickly evaluating available electrode combinations, such as by performing tests on respective user-selected electrode combinations and vectors. This can help the user to quickly and confidently configure an implantable medical device based on the results of such tests.

In an example, a user interface can include a graphical display. The graphical display can include a graphical representative image of the available electrodes as implanted in a body. In an example, a user interface can display available electrodes in a table. The tabular representation can include rows or columns that can be sorted by a user. The graphical or tabular representation of available electrodes enables the display of a large amount of information in a form that can be readily understood, manipulated, and used by a practitioner engaged in configuring the medical device. In an example, the graphical or tabular representation of available electrodes can include an interactive display of electrostimulation electrodes available for use in combination with a user-selected electrode. The interactive display of electrode combination information can facilitate device configuration for the practitioner by enabling the practitioner to program a device more easily and more efficiently than by manually selecting and testing each electrode combination.

The graphical or tabular user interface can be configured to receive a user's selection of a set of one or more electrode combinations from among the graphical or tabular representation of multiple available electrodes. The interface can be further configured to receive a selection of one or more tests to perform on the selected electrode combinations. The interface, which can be coupled to a processor, can then initiate a sequence of tests on the selected electrode combinations and receive a result of the one or more tests performed. The results, or information indicative of the results, can be displayed graphically or in text, and in visual correspondence with the original representation of the multiple available electrodes. Thus, the user is permitted to view the test results alongside the original test parameters. In an example, the results can further include a calculated comparison metric. In an example, the comparison metric can be used by a user to evaluate the relative performance of various electrode configurations. In an example, the comparison metric can be used by a processor to automatically select a desirable or "optimal" pacing vector. In an example, the automatically selected vector can be presented to a user, or can be automatically configured for use with an implantable medical device.

Example 1 includes subject matter (such as a method, a means for performing acts, or a machine-readable medium including instructions that, when performed by the machine, cause the machine to perform acts) that can include providing to a user an interactive representation of a first set of electrostimulation electrodes or vectors, receiving a first selection of an electrostimulation electrode or vector, providing a visual indication of the first selection using the interactive representation, and interactively using the first selection, wherein interactively using the first selection can include performing at least one of: providing, using the interactive representation, a second set of electro stimulation electrodes or vectors that is available for use with the first selection; displaying, using the interactive representation, information indicative of a parameter test result for an electrostimulation electrode combination or vector associated with the first selection; or, performing, using the interactive representation, interactive user-controllable parameter testing using the first selection.

In Example 2, the subject matter of Example 1 can optionally include interactively using the first selection, including providing a second set of electrostimulation electrodes or vectors that is available for use with the first selection.

In Example 3, the subject matter of one or any combination of Examples 1-2 can optionally include interactively using the first selection, including displaying information indicative of a parameter test result for an electrostimulation electrode combination or vector associated with the first selection.

In Example 4, the subject matter of one or any combination of Examples 1-3 can optionally include interactively using the first selection, including performing interactive user-controllable parameter testing using the first selection.

In Example 5, the subject matter of one or any combination of Examples 1-4 can optionally include interactively using the first selection, including providing, in visual correspondence with the first selection, a second set of electrostimulation electrodes or vectors that is available for use with the first selection.

In Example 6, the subject matter of one or any combination of Examples 1-5 can optionally include interactively using the first selection, including displaying information indicative of a parameter test result in visual correspondence with the electrode combination or vector associated with the result.

In Example 7, the subject matter of one or any combination of Examples 1-6 can optionally include displaying to a user an interactive representation of a first set of electrostimulation electrodes or vectors, including displaying a pictorial interactive representation of a set of electrostimulation electrodes or vectors, including a user-selectable representation of an electrostimulation electrode or vector.

In Example 8, the subject matter of one or any combination of Examples 1-7 can optionally include displaying to a user an interactive representation of a first set of electrostimulation electrodes or vectors, including displaying a tabular interactive representation of a set of electrostimulation electrodes or vectors, including a user-selectable table element representative of an electrostimulation electrode or vector.

In Example 9, the subject matter of one or any combination of Examples 1-8 can optionally include receiving a first selection of an electrostimulation electrode or vector, including receiving the first selection from a user using the interactive representation.

In Example 10, the subject matter of one or any combination of Examples 1-9 can optionally include displaying, using the interactive representation, information indicative of a parameter test result in substantially real-time.

In Example 11, the subject matter of one or any combination of Examples 1-10 can optionally include receiving from the user a second selection of an electrostimulation electrode or vector, selected from among the second set of electrostimulation electrodes or vectors, the second selection performed by the user using the interactive representation.

In Example 12, the subject matter of one or any combination of Examples 1-11 can optionally include programming an ambulatory medical device using one or more of the first selection or the second selection.

In Example 13, the subject matter of one or any combination of Examples 1-12 can optionally include providing to a user an interactive representation of a set of one or more parameter tests or parameter test characteristics.

In Example 14, the subject matter of one or any combination of Examples 1-13 can optionally include performing interactive user-controllable parameter testing including using a selection of a parameter test or parameter test characteristic received from the user.

In Example 15, the subject matter of one or any combination of Examples 1-14 can optionally include performing interactive user-controllable parameter testing, including adjusting subsequent parameter tests in response to a received parameter test result.

In Example 16, the subject matter of one or any combination of Examples 1-15 can optionally include receiving the first selection of an electrostimulation electrode or vector, including receiving a selection of an electrostimulation electrode or vector configured for intravascular delivery of electrostimulation energy to multiple locations at or near the left ventricle of the heart.

In Example 17, the subject matter of one or any combination of Examples 1-16 can optionally include calculating a comparison metric using the test result of an electrostimulation parameter test.

In Example 18, the subject matter of one or any combination of Examples 1-17 can optionally include using a comparison metric, including displaying the comparison metric, such as using the interactive display.

In Example 19, the subject matter of one or any combination of Examples 1-18 can optionally include using a comparison metric, including analyzing the comparison metric.

In Example 20, the subject matter of one or any combination of Examples 1-19 can optionally include using a comparison metric, including programming an ambulatory medical device.

In Example 21, the subject matter of one or any combination of Examples 1-20 can optionally include using a comparison metric, including organizing the displayed information indicative of a parameter test result.

Example 22 can include, or can be combined with the subject matter of one or any combination of Examples 1-21 to optionally include, subject matter such as an apparatus including a display configured to provide an interactive representation of a set of electrostimulation electrodes or vectors, wherein the interactive representation can include a first input, including an interactive visual indication indicating a first selection of an electrostimulation electrode or vector, and at least one of: an interactive visual indication, provided using the interactive representation, of a second set of electrostimulation electrodes or vectors that is available for use with the first selection; an interactive visual indication, displayed using the interactive representation, of information indicative of a parameter test result for an electrostimulation electrode combination or vector associated with the first selection; or, an interactive user-control, configured to perform, using the interactive representation, interactive user-controllable parameter testing using the first selection.

In Example 23, the subject matter of one or any combination of Examples 1-22 can optionally include an interactive representation including an interactive visual indication, provided using the interactive representation, of a second set of electrostimulation electrodes or vectors that is available for use with the first selection.

In Example 24, the subject matter of one or any combination of Examples 1-23 can optionally include an interactive representation including an interactive visual indication, displayed using the interactive representation, of information indicative of a parameter test result for an electrostimulation electrode combination or vector associated with the first selection.

In Example 25, the subject matter of one or any combination of Examples 1-24 can optionally include an interactive representation including an interactive user-control, configured to perform, using the interactive representation, interactive user-controllable parameter testing using the first selection.

In Example 26, the subject matter of one or any combination of Examples 1-25 can optionally include an interactive representation including an interactive visual indication of a second set of electrostimulation electrodes or vectors that is available for use with the first selection, the second set provided using the interactive representation and in visual correspondence with the first selection.

Example 27 can include, or can be combined with the subject matter of one or any combination of Examples 1-26 to optionally include, subject matter (such as a method, a means for performing acts, or a machine-readable medium including instructions that, when performed by the machine, cause the machine to perform acts) including providing to a user an interactive representation of a first set of electrostimulation electrodes or vectors, receiving from the user a first selection of an electrostimulation electrode or vector, the first selection performed by the user using the interactive representation, providing a visual indication of the first selection using the interactive representation, providing, using the first selection and the interactive representation, a second set of electrostimulation electrodes or vectors that is available for use with the first selection, displaying, using the first selection and the interactive representation, information indicative of a parameter test result for an electrostimulation electrode combination or vector associated with the first selection, and performing, using the first selection and the interactive representation, interactive user-controllable parameter testing using the first selection.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2B and FIG. 2C illustrate generally examples of graphical representations of vectors that can be established between two electrodes.

FIGS. 2D, 2E, 2F, 2G, 2H, 2I, 2J, 2K, 2L, 2M, 2N, and 2O, illustrate generally examples of graphical representations of vectors that can be established between three electrodes.

DETAILED DESCRIPTION

An interactive representation of electrostimulation electrodes or vectors can be provided, such as for configuring combinations of electrostimulation electrodes. In an example, electrodes or test parameters can be presented graphically or in a table. A user interface can be configured to receive user-input designating electrode combinations or vectors for test or for use in programming an implantable or ambulatory medical device. The interface can be used to indicate suggested electrode combinations or vectors in response to a first selection of an electrode. Tests can be performed on electrode combinations and vectors, and the results of the tests can be presented to a user using the interactive representation. In an example, test results can be analyzed by a processor and optionally used to program an implantable or ambulatory medical device.

Figure 1:
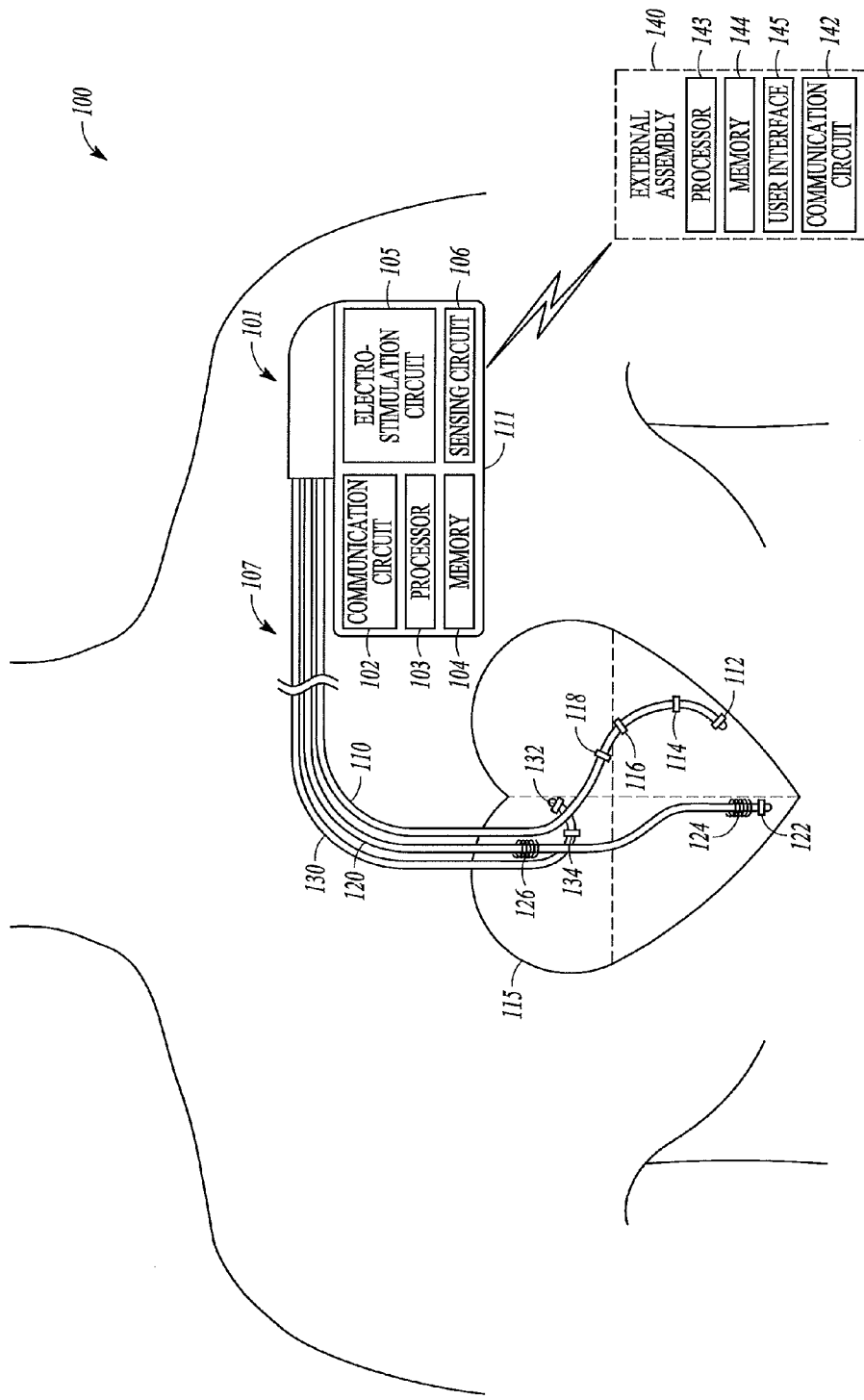
FIG. 1 illustrates generally an example of a portion of a system that can include an implantable or ambulatory medical device, one or more implantable leads, and an external assembly. The implantable or ambulatory medical device can be communicatively coupled to an external assembly.

FIG. 1 illustrates generally an example of a system 100 that can include an implantable or ambulatory medical device 101. The ambulatory medical device 101 can be coupled to one or more electrodes, which can be carried by one or more implantable leads, such as implantable leads 110, 120, and 130. The implantable leads 110, 120, and 130 can be configured to receive or sense electrical signals from the heart 115. The ambulatory medical device 101 can include a hermetically-sealed or similar housing 111. The housing 111 can include titanium or another biocompatible material, such as one or more other conductive materials.

In an example, the ambulatory medical device 101 can include one or more of a pacemaker, a defibrillator, an implantable monitor, a drug delivery device, a cardiac resynchronization therapy (CRT) device, a neural stimulation device, or one or more other implantable assemblies configured to monitor a person or configured to provide one or more treatments to the person. Examples of such monitoring or treatment can include electrostimulation of tissue such as cardiac tissue, or electrical monitoring of muscular or cardiac activity. In an example, the ambulatory medical device 101 can include an external medical device, such as a pacing system analyzer, or other external medical device that can be used to configure a system of multipolar implantable leads.

In the example of FIG. 1, the ambulatory medical device 101 can be coupled to a heart 115, or other body tissue, such as via the electrode system 107, epicardial electrodes, or external (e.g., skin-patch) electrodes. The electrode system 107 can include at least one lead and at least one electrode for each lead. FIG. 1 shows an example in which there are three implantable leads 110, 120, and 130. In the example of FIG. 1, the implantable lead 110 can be configured for use in association with a left ventricle of the heart 115. For example, the implantable lead 110 can be sized and shaped to allow insertion into a coronary sinus and intravascular advancement such as to put at least one electrode in association with the left ventricle of the heart. The implantable lead 110 can be a multipolar lead, including a plurality of electrodes and corresponding conductors. In an example, the implantable lead 110 can include four discrete electrodes, such as: a tip electrode 112, a first ring electrode 114, a second ring electrode 116, and a third ring electrode 118. In an example, the electrodes 114, 116, and 118 can be located near a distal portion of the implantable lead 110. Each of the electrodes 114, 116, and 118 can be separated by electrically insulating material, thus electrically isolating the individual electrodes. Each of the four left ventricular electrodes 112, 114, 116, and 118 can correspond to a unique electrical conductor and can be individually addressable by a sensing circuit 106 or an electrostimulation circuit 105 contained within the ambulatory medical device 101.

In the example of FIG. 1, the implantable lead 120 can include a tip electrode 122, a first coil electrode 124, and a second coil electrode 126. As generally shown in FIG. 1, the implantable lead 120 can, in an example, be inserted into the right atrium and right ventricle of the heart 115 so that the first coil electrode 124 is positioned in the right ventricle and the second coil electrode 126 is positioned in the right atrium.

In the example of FIG. 1, the implantable lead 130 can include a tip electrode 132 and a ring electrode 134. As generally shown in FIG. 1, the implantable lead 130 can be configured for insertion into the right atrium of the heart 115.

The physical illustration of the implantable leads 110, 120, and 130 provided in FIG. 1 is provided as an illustrative non-limiting example of leads that can correspond with displays similar to those displays shown in FIGS. 2A, 2P, 2Q, 3A, 3B, 4, 5, 6A, 6B, and 7, and discussed in more detail below.

The external assembly 140 can be an adjunct (e.g., non-ambulatory) external assembly. In an example, the external assembly 140 can include the ambulatory medical device 101 features described above and below, such that the external assembly 140 can be configured to be coupled to the electrode system 107. The ambulatory medical device 101 can be configured to communicate (wired or wirelessly) with a local or remote external device, such as external assembly 140. This can include using an RF, optical, acoustic, or other communication link. The external assembly 140 can be a portion or part of a patient management system. In an example, the external assembly 140 can communicate with one or more remote clients, such as web-based clients, or can be communicatively coupled to one or more servers, which can include medical and patient databases.

In an example, the ambulatory medical device 101 can include a communication circuit 102, a processor circuit 103, a memory circuit 104, an electrostimulation circuit 105, or a sensing circuit 106. The processor circuit 103 and memory circuit 104 can be used to control the operation of the ambulatory medical device 101. For example, the processor circuit 103 can be programmed to detect a cardiac condition, such as by using the sensing circuit 106 or another physiological sensor, and to respond to the detected cardiac condition, such as by using the electrostimulation circuit 105. The memory circuit 104 can include one or more parameters, such as for various pacing and sensing modes, test procedures or the like. The memory circuit 104 can be configured to store physiological data, such as data concerning the condition of the heart 115. The memory circuit 104 can be configured to store device data, such as data about a status of a test or a test result. In an example, the ambulatory medical device 101 can use the electrostimulation circuit 105 or the sensing circuit 106 to interface with the electrode system 107. The electrostimulation circuit 105 or the sensing circuit 106 can be configured to generate an electrostimulation signal, the electrostimulation circuit 105 or the sensing circuit 106 can be electrically coupled to the electrode system 107, and the electrostimulation signal can be transmitted from the electrostimulation circuit 105 or the sensing circuit 106 to the heart 115 via the electrode system 107. The communication circuit 102 can be configured to establish a data communication link between the ambulatory medical device 101 and the external assembly 140.

The external assembly 140 can include a communication circuit 142, a processor circuit 143, a memory circuit 144, or a user interface 145. In an example, the communication circuit 142 can include inductive coils or radio frequency telemetry circuitry, and can be configured to communicate with the ambulatory medical device 101. The processor circuit 143 and memory circuit 144 can be used to interpret information received from the user interface 145, or can be used to determine when to use the communication circuit 142 to exchange information with the ambulatory medical device 101. In an example, the processor circuit 143 and memory circuit 144 can be used to initiate an electrostimulation test performed by the external assembly 140 using the electrode system 107. The external assembly 140 can be used to perform electrostimulation tests using the electrode system 107 and can be configured to display results such as by using the user interface 145.

In the example of FIG. 1, the user interface 145 can include, but is not limited to, a keyboard, a mouse, a light pen, a touch-screen, a display screen, a printer, or an audio speaker. In an example, the user interface 145 can be configured as a full color, high definition graphical display, such as using an LCD computer monitor. In an example, the user interface 145 can be configured for use as a monochromatic display, such as using a CRT monitor to display text. In an example, the user interface 145 can be configured to interactively present a graphical representation of electrostimulation electrodes or vectors to a user. In another example, the user interface 145 can be configured to interactively present a text-based representation of electrostimulation electrodes or vectors.

In an example, the user interface 145 can be configured to provide an interactive representation of a first set of electrostimulation electrodes or vectors. In an example, a user or a processor-executed algorithm can use the interactive representation to select a first electrostimulation electrode or vector. For example, the processor-executed algorithm can be configured to determine a default or nominal first electrostimulation electrode selection, and to present the electrode to a user for confirmation or further instruction. The interactive representation can be configured to display an indication of the first selection, such as by highlighting the selection on the display screen. In an example, the interactive representation can provide a second set of electrostimulation electrodes or vectors. The second set can be provided in response to a first selection by a user. The second set can include only those electrostimulation electrodes or vectors that are available for use with the first selection. The electrostimulation electrodes or vectors that are available for use with the first selection can include all multipolar vectors that incorporate, at least in part, the electrostimulation electrode of the first selection. In an example, a touch-screen implementation of the user interface 145, shown, for example, in FIG. 2A, can be used to define several electrostimulation vectors, such as by a user touching on the display screen graphical representations of multiple electrodes, such as in a particular sequence. Predefined vectors, such as a category of vectors (e.g. all bipolar pacing vectors, or all unipolar sensing vectors) can be presented for selection by a user using the interactive representation. This can be helpful in that the user need not select individual electrostimulation electrodes to manually configure a vector or set of vectors. In an example, the user can electively modify a predefined vector, such as by incorporating additional electrostimulation electrodes, or removing one or more electrostimulation electrodes from the predefined vector.

In an example, electrostimulation parameter tests can be initiated using the interactive representation. Results of the parameter tests can be displayed using the interactive representation, such as to display raw data or information indicative of a parameter test result, such as a calculated comparison metric. The results can be displayed in visual correspondence with the interactive representation of the electrostimulation electrode or vector associated with the test result.

In an example, the interactive representation can be used to program the ambulatory medical device 101, such as by selecting an electrostimulation electrode, or an electrostimulation electrode combination or vector, and configuring the electrostimulation electrode, electrostimulation electrode combination, or vector for use with the ambulatory medical device 101. In an example, the interactive representation can be used to store configuration information, such as by using the external assembly 140 and the memory circuit 144. Stored configuration information can be transmitted to an ambulatory or implantable medical device. In an example, the external assembly 140 can be used to determine an optimal pacing configuration. During or after implantation, the optimal pacing configuration can be wirelessly transmitted to the ambulatory medical device 101.

Figure 2A:
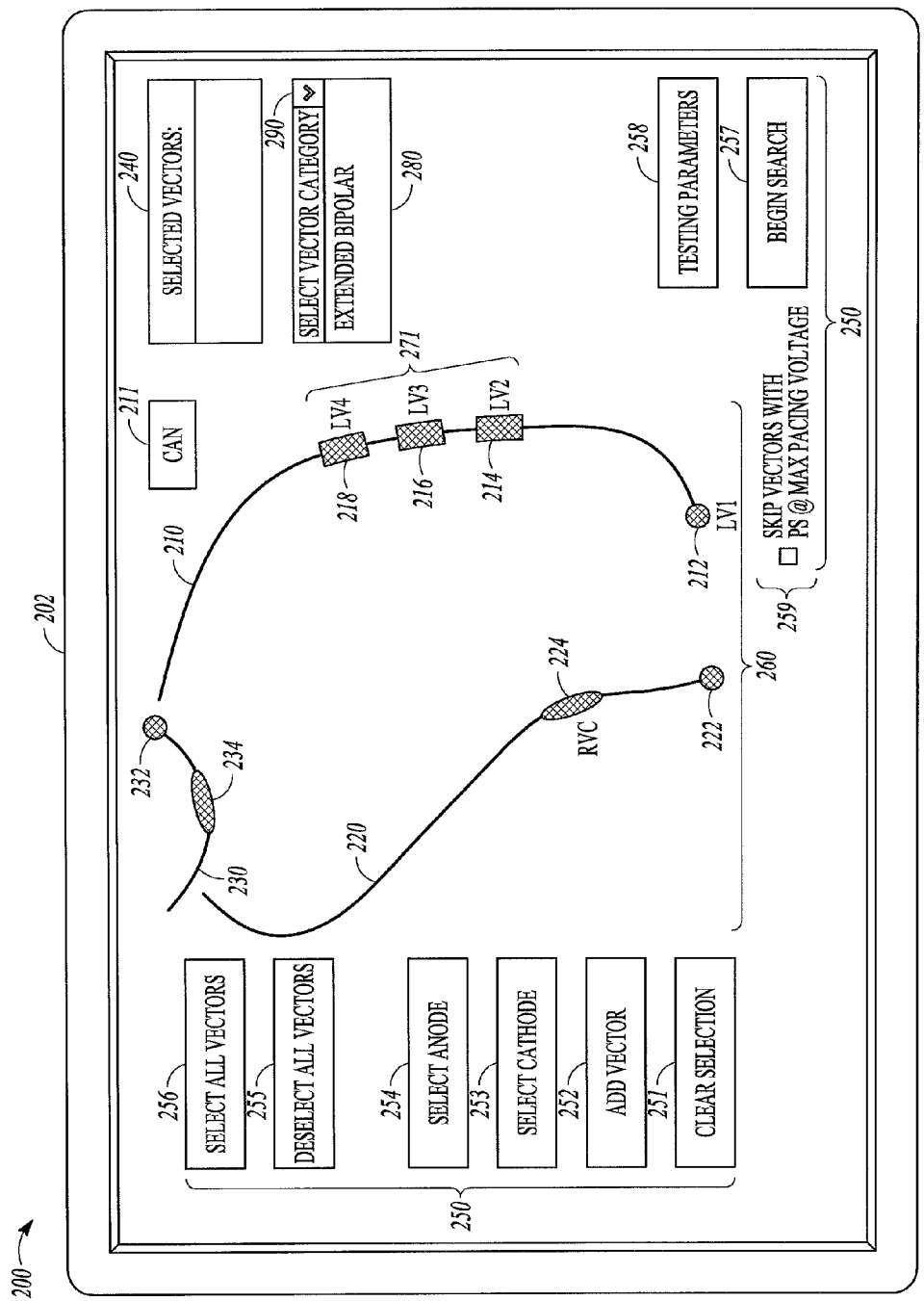
FIG. 2A illustrates generally an example of a portion of a system that can include a pictorial interactive representation of electrodes.

FIG. 2A is a diagram illustrating generally an example of a user interface 200 comprising an interactive user interface display 202. The user interface 145 can be configured to present the interactive user interface display 202 to a user. The interactive user interface display 202 can include a Selected Vectors region 240. The Selected Vectors region 240 can be used to interactively display a representation of a user-selection of electrostimulation electrode combinations or vectors. The interactive user interface display 202 can also include a set of buttons 250, and an interactive representation of electrostimulation electrodes 260. The set of buttons 250 can be presented as selectable elements on the user interface screen. The set of buttons 250 can correspond to a keyboard or other hardware input device. The interactive user interface display 202 can include a Select Vector Category region 280. The interactive representation of electrostimulation electrodes 260 can include a pictorial interactive representation of a set of electrostimulation electrodes or vectors, such as including the electrostimulation electrodes that can be coupled to the ambulatory medical device 101.

The interactive user interface display 202 can be used to configure electrostimulation vectors, such as pacing, sensing, or shock vectors, among others, for use by the ambulatory medical device 101. The ambulatory medical device 101 can be electrically coupled to the electrode system 107, which can include a set of one or more multipolar leads. An interactive representation of electrostimulation electrode combinations or vectors 260 of the electrode system 107 can be displayed graphically, such as by using pictorial representations of electrodes, leads, and vectors. A user can select the number and type of leads included in the electrode system 107, such as by using the interactive user interface display 202. In an example, the number and type of leads included in the electrode system 107 can be automatically recognized by a processor-executed algorithm, such as by using the processor circuit 103 or the processor circuit 143.

A clinician may want to configure the ambulatory medical device 101, such as to effectively and efficiently pace a heart using the set of multipolar leads. However, the multipolar leads can include several electrostimulation electrodes per lead and, therefore, the set of pacing and sensing configurations available to the clinician can be numerous. It can be a lengthy and cumbersome task for the clinician to define and test each potential pacing or sensing configuration, such as for efficacy and efficiency. In the example of FIG. 2A, a clinician can use the interactive user interface display 202 to quickly view available pacing configurations, to determine which pacing configurations to test, to select those configurations, to test the selected configurations, and to confidently program the ambulatory medical device 101 using the results of the tests.

FIGS. 2B through 2O illustrate an example of the difficulty a clinician may encounter in configuring an ambulatory medical device to use multipolar leads. FIGS. 2B and 2C illustrate the case of a first electrode A and a second electrode B. In an example, electrode A can be the conductive housing electrode 211 of the ambulatory medical device 101 and electrode B can be a left ventricular ring electrode 214. In the example of FIGS. 2B and 2C, there are two possible combinations of the two electrostimulation electrodes and therefore there are two vectors. The first is the vector shown in FIG. 2B, wherein the anode is chosen to be electrode A, the cathode is chosen to be electrode B, and an arrow represents the electrostimulation vector from cathode B to anode A. The second possible combination is shown in FIG. 2C, where the anode is electrode B, the cathode is electrode A, and the arrow represents the electrostimulation vector from cathode A to anode B. In the examples of FIG. 2B and FIG. 2C, the arrowhead can be configured to point toward the anode.

FIGS. 2D, 2E, 2F, 2G, 2H, 2I, 2J, 2K, 2L, 2M, 2N, and 2O illustrate the case of three electrostimulation electrodes represented by a first electrode A, a second electrode B, and a third electrode C. In an illustrative example, the first electrode A can be the left ventricular tip electrode 212, the second electrode B can be the left ventricular ring electrode 214, and the third electrode C can be the conductive housing electrode 211 of the ambulatory medical device 101. One skilled in the art can appreciate that twelve distinct combinations of electrodes A, B, and C are possible, and those twelve combinations define twelve unique electrostimulation vectors. FIGS. 2D, 2E, 2F, 2J, 2K, and 2L illustrate generally the bipolar vectors that can be formed by utilizing only two of the three available electrodes. FIG. 2G illustrates an example of a vector wherein electrostimulation electrodes A and B are electrically coupled to form the cathode, and the anode is electrode C. Similarly, other possible multipolar vectors are graphically illustrated in FIGS. 2H, 2I, 2M, 2N and 2O. The present inventors have recognized that the introduction of a fourth (or even further) electrode will increase the number of potential electrostimulation electrode combinations or vectors in a nonlinear fashion such that it would inconvenience a clinician to manually program and test each vector.

In the example of FIG. 2A, the interactive representation of electrostimulation electrodes 260 can include generally a graphical indication of the relative locations of two or more electrostimulation electrodes with respect to each other. The interactive representation of electrostimulation electrodes 260 can be configured to represent graphically an actual or proposed configuration of implantable leads and electrodes. A multipolar left ventricular lead, such as implantable lead 210, can be displayed. The multipolar left ventricular lead can be displayed if a left ventricular lead is available for use by or compatible with the ambulatory medical device 101. A left ventricular lead displayed using the interactive representation of electrostimulation electrodes 260 can be configured to display a representation of the electrodes associated with the left ventricular lead. The representation of the electrodes can be displayed in association with a representation of an implantable lead, such as overlaid on a line segment representing the implantable lead. A representation of an implantable lead configured for application in a right ventricular area of the heart can include a representation of the electrodes present at the distal end of the implantable lead. The interactive representation of electrostimulation electrodes 260 can graphically represent the relative locations of two or more electrostimulation electrodes as they are implanted in a host body.

In an example, the interactive representation of electrostimulation electrodes 260 can include a graphical representation of a right ventricular lead 220 comprising a right ventricular tip electrode 222, and a right ventricular defibrillation coil electrode 224. The representation of the right ventricular lead 220 can include displaying a line segment. The representation of a right ventricular tip electrode 222 can include displaying an icon in association with the line segment, such as overlaying the line segment. In the example of FIG. 2A, the interactive representation of electrostimulation electrodes 260 can include a graphical representation of a left ventricular lead 210 comprising a left ventricular tip electrode 212 at the distal end of the lead, and three ring electrodes 214, 216, and 218, the three ring electrodes positioned in the left ventricle of the heart. Each of the ring electrodes 214, 216, and 218 can be electrically isolated from one another and can be individually addressable by the ambulatory medical device 101, or by the external assembly 140, such as described above in the discussion of FIG. 1. The interactive representation of electrostimulation electrodes 260 can further include an atrial electrode 230 comprising a tip electrode 232 and a coil electrode 234.

In the example of FIG. 2A, the graphical representation of a tip electrostimulation electrode (e.g. electrode 222) can include a circular icon. The graphical representation of a ring electrostimulation electrode (e.g. ring electrode 214) can include a rectangular icon. The graphical representation of a coil electrostimulation electrode (e.g. electrode 234) can include an oval icon. The interactive representation of electrostimulation electrodes 260 can further include a graphical representation of the conductive housing electrode 211, or the "can" of the ambulatory medical device 101, including a rectangle with rounded edges. The individual electrostimulation electrodes (e.g. electrodes 214, 222, 234, etc.) can be selectable, such as using a computer mouse or touch screen to permit a user to select individual electrodes, or to select electrodes on a particular lead. For example, a user can select the right ventricular tip electrode 222. In another example, a user can select all of the available electrodes on the left ventricular lead 210.

In an example, the graphical representations of leads and electrodes can be configured to use several colors. For example, a particular color can be used to display the left ventricular lead 210, a second color to display the tip electrode 212 and ring electrodes 214, 216, and 218 in association with the left ventricular lead, a third color to display the right ventricular lead 220, and so forth. Each of the electrodes can be displayed using a different color. A user of the interactive user interface display 202 can elect to enter designation information 271, either as text or a graphic, in the vicinity of the graphical representation of the implantable leads. Designation information 271 can be used to add, for example, names or designators to each of the electrodes. The designation information 271 can be entered by a user, such as by selecting an electrode icon by double-clicking. The designation information 271 can include factory pre-set information or can be generated in response to a detected lead configuration. In the example of FIG. 2A, the electrostimulation electrodes on the left ventricular lead can be designated "LV1," "LV2," "LV3," and "LV4," and the coil electrostimulation electrode on the right ventricular lead can be designated "RVC." Each of the electrodes displayed using the interactive representation of electrostimulation electrodes 260 can include unique designation information 271, or the designation information 271 can be omitted from any electrode. Such on-screen designations can be useful to a clinician or group of clinicians who need to easily refer to a plurality of electrodes. Designation information 271 can be added to the implantable leads.

Figure 2P:
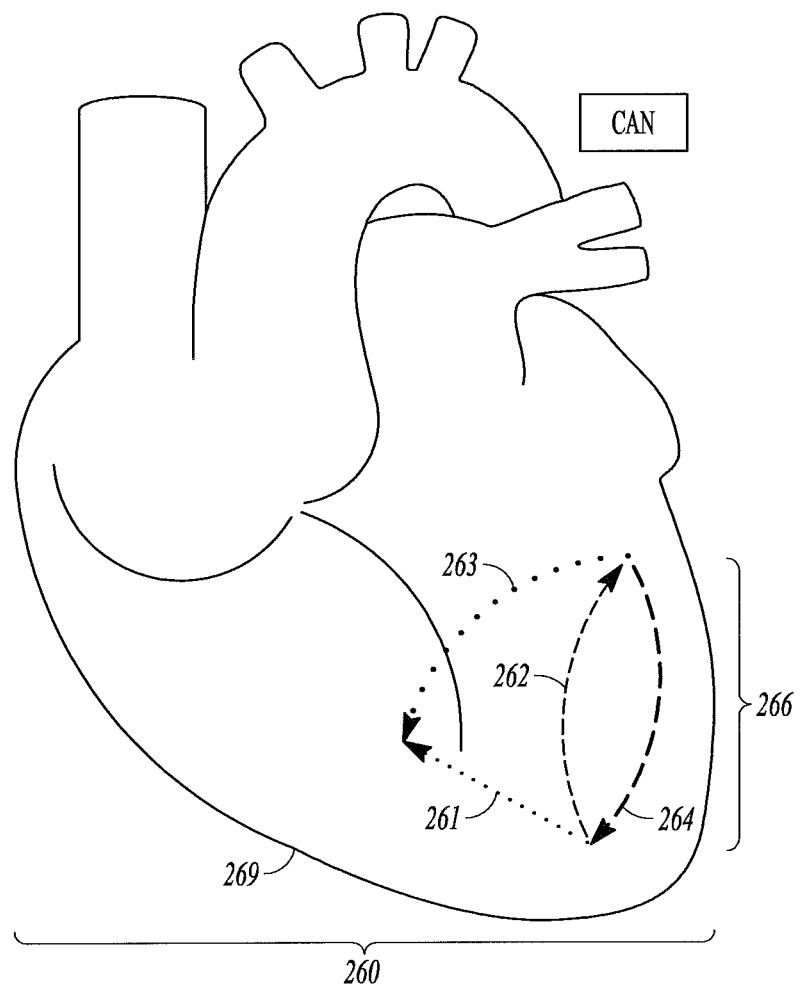
FIG. 2P illustrates generally an example of a portion of a system that can include a pictorial interactive representation of electrostimulation vectors.

FIG. 2P illustrates generally an example of the interactive representation of electrostimulation electrodes 260 including a graphical indication of one or more electrostimulation vectors presented without the graphical indication of individual electrostimulation electrodes. A graphical representation of an electrostimulation vector can be presented, such as using an arrow symbol. The display can omit discrete electrodes and can display multiple vectors, or can display a combination of vectors and discrete electrodes. Displayed vectors 266 can be superimposed over an image of a heart 269 such as to provide visual context to the relative locations of the displayed vectors. The displayed vectors 266 can be shown in situ as they correspond to energy sensing locations or energy delivery locations within or relative to a heart. The image of a heart can be rotated in a virtual three dimensional space on a display screen to permit a clinician to "see" a vector and the physical heart region associated with the vector. One or more vectors can be displayed relative to one another, and the displayed vectors can be distinguished such as using visual features including variable lengths, widths, or colors, among others. The vectors 262 and 264 can represent bipolar pacing vectors, such as using two electrodes on an implantable lead configured for implantation at or near a left ventricle of a heart.

In the example of FIG. 2A, a set of user-selectable buttons 250 or selectable elements can be made available to a user, such as for selection by a mouse or a touch-screen input. In an example in which the set of buttons 250 include buttons displayed on a display screen, the buttons can include selectable rectangles with descriptive text superimposed. The size and shape of the buttons and the associated descriptive text, if any, can vary, such as according to the capabilities or limits of the display screen and operating system.

In an example, the set of buttons 250 can include an "Add Vector" button 252. A user can select the "Add Vector" button 252, such as to call up a pop-up window or the like to permit the user to enter one or more parameters, such as to define an electrostimulation or sensing vector. A user selection can indicate a category of electrodes or vectors, such as all vector combinations associated with a particular electrode. The Select Vector Category region 280 can display categories of vectors available to a user. In an example, all extended bipolar vectors can be selected. The different categories of vectors can be presented in a drop-down box. A drop-down box can be indicated using an icon 290 showing a square surrounding a triangle.

In an example, a category of vectors can include bipolar pacing vectors associated with electrode "LV1." In the example of FIG. 2A, the category of vectors including bipolar pacing vectors associated with electrode "LV1" can include the vectors LV1>>LV2, LV2>>LV1, LV1>>LV3, LV3>>LV1, etc. The Select Vector Category region 280 can thus enable selection of a large number of vectors without requiring a user to manually configure each vector.

Figure 2Q:
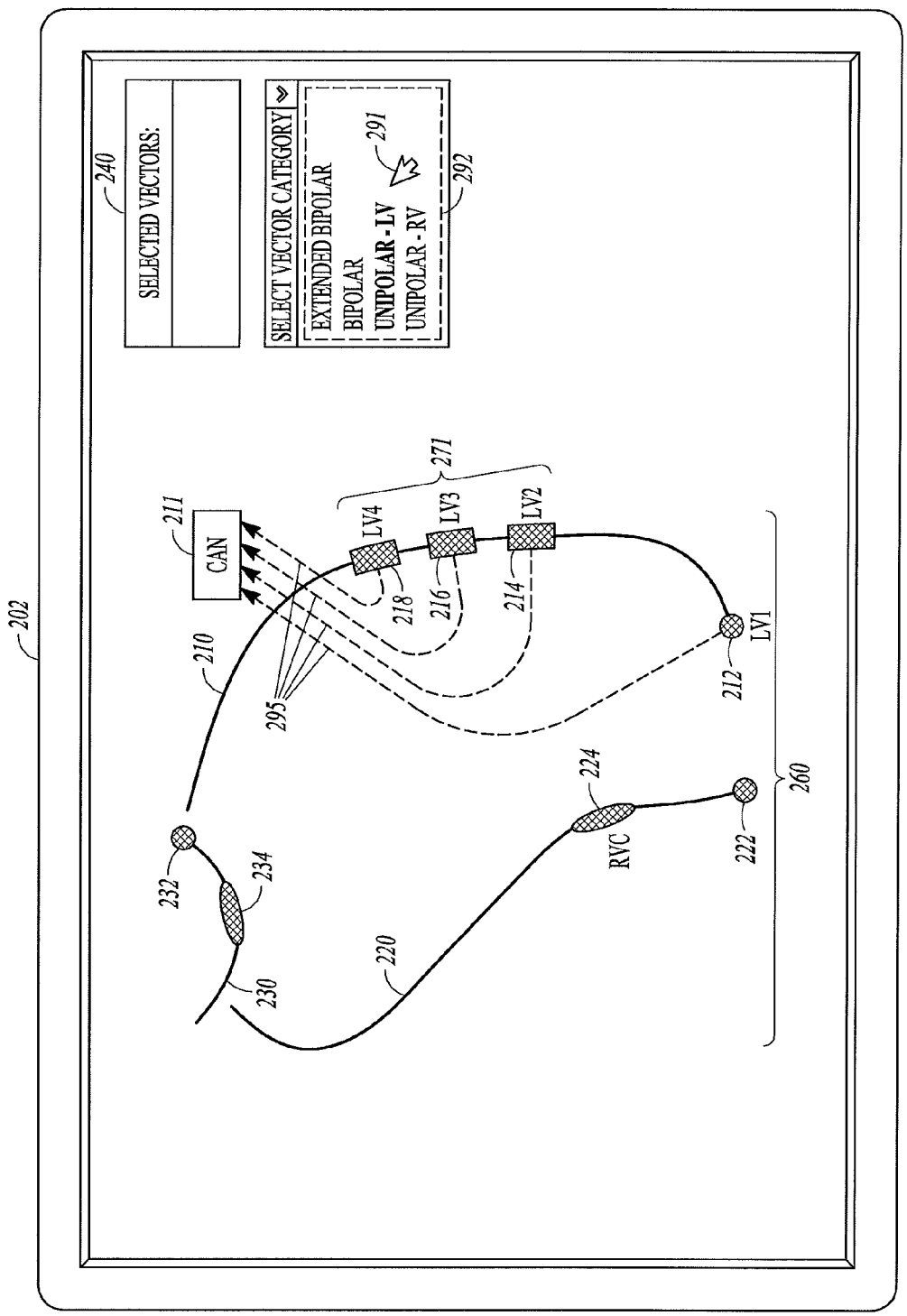
FIG. 2Q illustrates generally an example of a portion of a system that can include a pictorial interactive representation of a selection of multiple electrostimulation electrode combinations or vectors.

In an example, a user selection can indicate an automatically-generated set of electrode combinations or vectors. FIG. 2Q illustrates graphically an example in which unipolar vectors associated with electrodes disposed on the left ventricular lead 210 can be selected using the Select Vector Category region 280. A user can select the icon 290 to show a drop-down box 292. The drop-down box 292 can include a list of available categories of vectors. In an example, a user can select, such as using an arrow controlled by a mouse, "Unipolar—LV" to indicate a selection of unipolar vectors associated with electrodes disposed on the left ventricular lead 210. The set of vectors associated with the selection can be indicated using the interactive representation of electrostimulation electrodes 260, such as by displaying arrows representative of the set of vectors 295.

The set of buttons 250 can include a "Select All Vectors" button 256, such as to responsively select all available vectors in a given configuration of the ambulatory medical device 101 and an associated electrode system 107. In an example, all available sensing vectors can be found automatically by the ambulatory medical device 101, such as by detecting the presence and type of leads connected to the device. In an example, all available pacing vectors can be found automatically by a processor-executed algorithm in the external assembly 140. In an example, the processor-executed algorithm can be configured to receive a user input defining the number and type of electrodes coupled to the ambulatory medical device 101. In the example of FIGS. 2D through 2O, the selection of the "Select All Vectors" button 256 can indicate an automatic selection of all twelve possible vectors associated with the combinations of electrostimulation electrodes A, B, and C. A graphical representation of the twelve selected vectors can then be presented to the user, such as using the interactive representation of electrostimulation electrodes 260 or the Selected Vectors region 240 of the interactive user interface display 202. In an example, a user can designate one or more electrodes to be omitted from the set of vectors generated in response to a user selection of the "Select All Vectors" button 256. An electrode can be designated for omission such as by clicking on an "X" icon associated with the graphical representation of the electrode.

The selected vectors can be represented in list form in a portion of the display, such as in the Selected Vectors region

240. The Selected Vectors region 240 can represent a test queue or test sequence. The test sequence presented in the Selected Vectors region 240 can be sortable by a user, such as by clicking on a representation of a vector and dragging the representation to the desired location in the test sequence.

The set of buttons 250 can include a "Deselect All Vectors" button 255 such as to automatically deselect all vectors. For example, a user may have already chosen the "Select All Vectors" button 256 and now wants to remove all vectors from the test queue. A user's selection of the "Deselect All Vectors" button 255 can clear the test queue. The set of buttons 250 can include a "Clear Selection" button 251. A user's selection of the "Clear Selection" button 251 can indicate that a presently selected vector or electrode is to be removed from the test queue. The selection of the "Clear Selection" button 251 can indicate that a selected area of the screen, such as the designation information 271 corresponding to the electrodes, is to be removed from the display. Other regions of the display, including the Selected Vectors region 240 or the Select Vector Category region 280 can be optionally removed from the interactive user interface display 202.

The set of buttons 250 can include a "Select Anode(s)" button 254 to indicate that a previously or subsequently selected electrostimulation electrode is to be used, at least in part, as the anode of an electrostimulation electrode combination or vector. The set of buttons 250 can include a "Select Cathode(s)" button 253 to indicate that a previously or subsequently selected electrostimulation electrode is to be used, at least in part, as the cathode of an electrostimulation vector.

The set of buttons 250 can include a "Testing Parameters" button 258 to prompt a user for pacing parameter information. In an example, a user's selection of the "Testing Parameters" button 258 can initiate a prompt presenting a set of pacing parameter tests or test characteristics, or can initiate a prompt to enter information regarding parameters such as pacing voltage level or pacing signal duration. The selection of the "Testing Parameters" button 258 can display a new window. The new window can present a list of available test parameters. The available test parameters can include left ventricular capture threshold, intrinsic amplitude, the presence of phrenic nerve stimulation, atrioventricular delay, right ventricular latency timing, and impedance, among others. The available test parameters can include a set of tests, or a range of test parameter values.

The set of buttons 250 can include a checkbox 259. In the example of FIG. 2A, the checkbox 259 can correspond to an indication to the system not to continue testing electrostimulation vectors where phrenic nerve stimulation is detected at the maximum pacing or test voltage level.

The set of buttons 250 can include a "Begin Search" button 257. Selection of the "Begin Search" button 257 can indicate that the system will automatically detect the available electrostimulation electrodes and populate the graphical display. Selection of the "Begin Search" button 257 can indicate that tests should commence on the selected vectors shown in the Selected Vectors region 240, or on the interactive representation of electrostimulation electrodes 260.

A user can use the user interface 200 to select an electrostimulation vector, such as by the steps: (1) selecting the "Select Anode(s)" button 254, (2) selecting a first electrostimulation electrode from the interactive representation of electrostimulation electrodes 260 (e.g. the left ventricular tip electrode 212), (3) selecting the "Select Cathode(s)" button 253, (4) selecting a second electrostimulation electrode from the interactive representation of electrostimulation electrodes 260 (e.g. the left ventricular ring electrode 214.) A user can select an additional electrostimulation vector by selecting the "Add Vector" button 252, and then repeating steps 1-4. The sequence of steps presented here and elsewhere in this document are intended to be exemplary only. Multiple permutations of the presented sequences can be made available to a user to achieve the same result. For example, a user could select a first electrostimulation electrode before selecting the "Select Anode(s)" button 254 to confirm the selection.

In an example, a user can use the user interface 200 to select all available electrostimulation vectors such as by selecting the "Select All Vectors" button 256. A list of selected vectors, such as in the Selected Vectors region 240, can be populated as the user adds vectors. The Selected Vectors region 240 can include a scrolling window to accommodate a list of selected vectors that exceeds the space available in the Selected Vectors region 240.

Figure 3A:
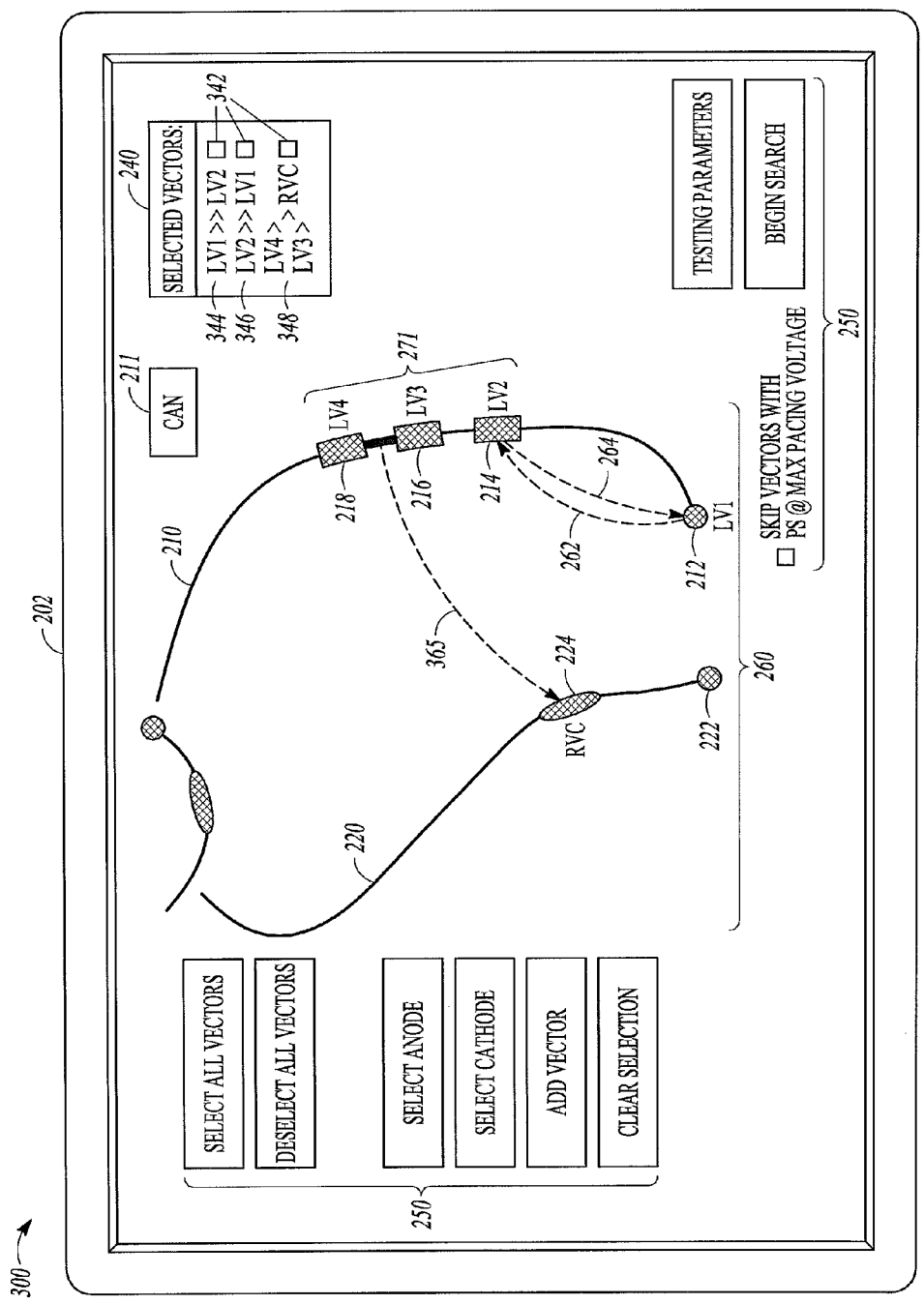
FIG. 3A illustrates generally an example of a portion of a system that can include a pictorial interactive representation of a combination of electrostimulation electrodes.

FIG. 3A is a diagram illustrating generally an example of a system 300 comprising an interactive user interface display 202. In an example, a user can select from the interactive representation of electrostimulation electrodes 260 one or more electrodes or vectors to designate for test or for programming an implantable medical device, among other functions. The interactive user interface display 202 can indicate several electrostimulation electrode combinations for test.

Multiple symbols can be used to pictorially graphically represent a vector, and the anode or cathode associated with that vector, to be tested. In an example, an arrowhead and a dotted line tail can pictorially graphically represent a vector to be tested. In an example, a plus sign (+) and a minus sign (−) can pictorially graphically represent an anode and cathode, respectively. A user can follow the steps presented above in the discussion of FIG. 2A to indicate that a left ventricular tip electrode 212, designated LV1, is to be used as a cathode, and a first left ventricular ring electrode 214, designated LV2, is to be used as an anode, defining a first vector 262. A user can further indicate a second vector 264 by selecting electrode LV2 as an anode and electrode LV1 as an anode. The first and second vectors can be graphically indicated on the interactive user interface display 202 by a dotted line extending from the cathode and terminating in an arrowhead pointing toward the anode. The graphical indication of a vector can be shown using the interactive representation in response to a user selection, such as immediately after receiving the user selection.

In an example, the Selected Vectors region 240 can indicate the selected vectors in list form. The first vector LV1>>LV2 can be represented in the Selected Vectors window at 344, and the second vector LV2>>LV1 is represented in the Selected Vectors window at 346. The graphical representation of selected electrodes can be configured to respond to a user selection such as changing the displayed icon representative of an electrode. The displayed icon can be highlighted, displayed in bolder fonts or colors, or can be enlarged, among other visual changes, to indicate a selection. A selected electrode or vector can have a different color than an unselected electrode or vector. The graphical representations of unselected vectors can be presented in different colors. A user can select a vector, such as by right clicking, such as to bring up a functional menu. The functional menu can include functions usable to manipulate a vector, such as by selecting a different anode or cathode, or to delete a vector. An icon can be displayed adjacent to each graphical representation of a vector. A user can select the icon, such as by using a mouse, to delete the vector.

The interactive user interface display 202 can respond to a first user selection of an electrostimulation electrode such as by providing, via a visual indication, a set of electrostimulation electrodes or electrostimulation electrode combinations available for use with the first selection. A visual indication of a set of electrostimulation electrodes or electrostimulation electrode combinations available for use with the first selection can include highlighting available electrodes, or displaying available vectors in response to the first selection. Highlighting available electrodes or displaying available vectors can include displaying electrodes or vectors in color, using animation such as a blinking electrode icon, or otherwise visually obviating the portion of the display associated with the available electrodes or vectors.

Figure 3B:
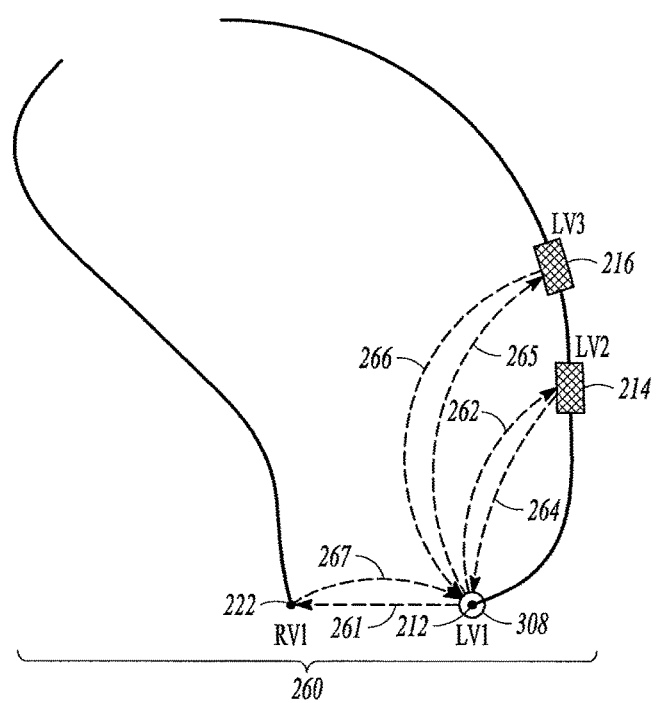
FIG. 3B illustrates generally an example of a portion of a system that can include a pictorial interactive representation of a set of electrostimulation electrodes or vectors which can be presented in response to a user selection.

FIG. 3B illustrates generally an example of the interactive representation of electrostimulation electrodes 260. For example, the left ventricular tip electrode 212, or "LV1," can be a first selection. The selection can be visually indicated such as by displaying a circle 308 around the selected electrode, or highlighting the selection using a background color under the graphical representation of the left ventricular tip electrode 212. In response to the first selection of LV1, the set of vectors 261, 262, 263, 264, 265, 266, and 267 can be automatically determined by the processor circuit 143 or the processor circuit 103 and displayed using the interactive user interface display 202. The set of vectors 261, 262, 263, 264, 265, 266, and 267 can automatically populate the Selected Vectors region 240 in response to receiving the first selection of the left ventricular tip electrode 212.

In an example, a multipolar electrostimulation electrode combination, or multi-site vector, can be established. For example, two or more electrodes can be electrically coupled together to form a single electrostimulation electrode node. In the example of FIG. 3A, the second left ventricular ring electrode 216, designated LV3, and a third left ventricular ring electrode 218, designated LV4, can be coupled together, as graphically indicated in the example of FIG. 3A by a bold line between the electrodes LV3 and LV4. The graphical indication that two or more electrodes are electrically coupled can be shown, such as by displaying coupled electrodes in a particular color or set of colors, and displaying uncoupled electrodes in another color. In the example of FIG. 3A, the combination of electrostimulation electrodes LV3 and LV4 can form the cathode and the right ventricular electrostimulation coil electrode 224, designated RVC, can form the anode of an electrostimulation vector. Such a multipolar, or multi-site, electrostimulation vector can be indicated in the Selected Vectors region 240, such as at 348. A multipolar electrostimulation vector can be indicated in the Selected Vectors region using text. The following formats, among others, can be used to indicate a multipolar electrostimulation vector using text:

$[_{LV3}{}^{LV4}\text{>RVC}]$; or

[LV4·LV3>>RVC]; or

[(LV4,LV3)>>RVC], etc.

The above text-based examples can be extended to accommodate any number of electrodes at the anode or cathode of an electrostimulation electrode combination.

In an example, the multipolar electrostimulation vector comprising electrodes LV3, LV4, and RVC can be defined by following the steps including: (1) selecting the "Add Vector" button from among the set of buttons 250 to indicate the entry of a new vector, (2) selecting the "Select Anode(s)" button from among the set of buttons 250, (3) selecting the right ventricular electrostimulation coil electrode 224, (4) selecting the "Select Cathode(s)" button from among the set of buttons 250, (5) selecting the second left ventricular ring electrode 216, (6) selecting the "Select Cathode(s)" button from among the set of buttons 250, (7) selecting the third left ventricular ring electrode 218, and (8) selecting the "Add Vector" button from among the set of buttons 250 to indicate the completion of the entry. In an example, the multipolar electrostimulation vector comprising electrodes LV3, LV4, and RVC can be defined by following the steps including: (1) selecting the right ventricular electrostimulation coil electrode 224 using a left-mouse click, (2) selecting the second left ventricular ring electrode 216 using a right-mouse click, and (3) selecting the third left ventricular ring electrode 218 using a second right-mouse click. There are a multitude of available patterns that can indicate the selection of a multipolar vector using the interactive representation of electrostimulation electrodes 260 and the other features available on the interactive user interface display 202. For example, if a touch screen is used to display the user interface 145, a touch-and-hold command can be used instead of a right-mouse click.

Checkboxes 342, corresponding to the individual vectors shown in the Selected Vectors region 240, can be shown. In an example, the checkboxes 342 can be used to designate a particular vector or set of vectors for deletion, such as using the "Clear Selection" button 251. In an example, the checkboxes can be used to designate a subset of selected vectors for a particular test.

Figure 4:
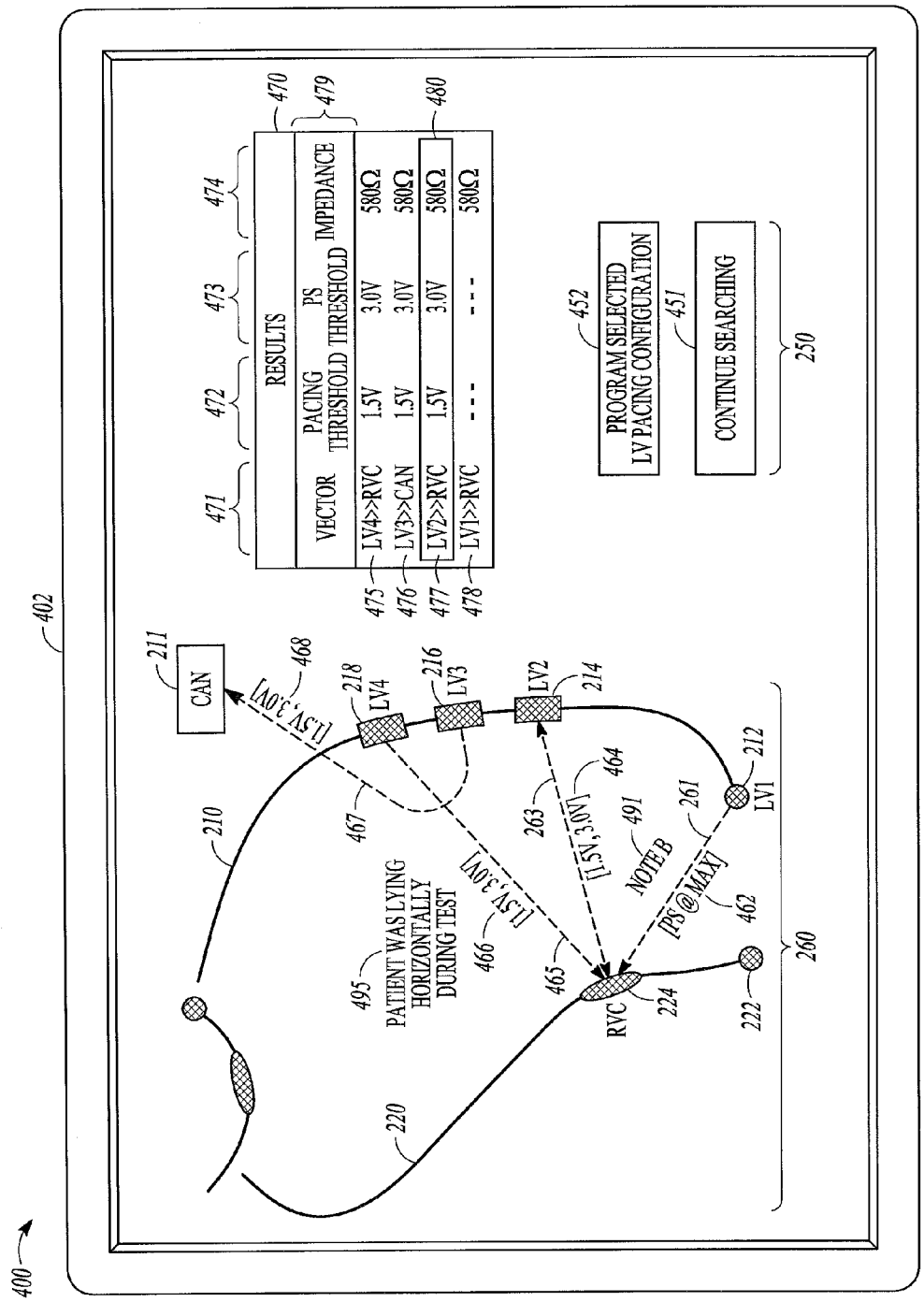
FIG. 4 illustrates generally an example of a portion of a system that can include a pictorial interactive representation of an indication of results of an electrostimulation parameter test.

FIG. 4 is a diagram illustrating generally an example of a system 400 including an interactive user interface display 402. The interactive user interface display 402 can include, among other features, a set of buttons 250, the graphical representation of electrostimulation electrodes 260, and a Results region 470.

The graphical representation of electrostimulation electrodes 260 can include a graphical representation of previously tested electrostimulation electrode combinations or vectors. The graphical representation of electrostimulation electrodes 260 can include a graphical representation of electrostimulation electrode combinations or vectors actively undergoing test. The interactive user interface display 402 can be configured to be displayed in response to commencement of a test sequence. The graphical representation of previously tested electrostimulation electrode combinations or vectors can include dotted lines and arrowheads to pictorially represent the tested vectors. The test results can be displayed in visual correspondence with the graphical representation of the vector. For example, a first electrostimulation vector 465, represented by an arrow symbol, can include the right ventricular coil electrode 224, designated "RVC," at the anode and the left ventricular ring electrode 218, designated "LV4," at the cathode. Results of pacing parameter tests can be overlaid with the graphical representation of electrostimulation electrodes 260, such as at a test result display location 466. The test result display location 466 can be located at or near the arrow symbol used to graphically represent a corresponding vector. A test result can be displayed in text and enclosed in brackets, offset from but in visual correspondence with the graphical representation of the vector (see FIG. 4 at 462, 464, 466, or 468).

The results of the pacing parameter test can be displayed in a Results region 470 on the interactive user interface display 402. The results corresponding to the first electrostimulation vector 465 can be displayed in the Results region 470 such as in a first row 475. The information displayed in the Results region 470 can be information indicative of a test result, such as pass or fail information instead of raw data. Information indicative of a test result can include raw numerical data, or a comparison metric associated with a particular range of numerical data, among others.

Test result information, such as the information presented in Results region 470, can be presented on a display in real-time as tests are being performed. A sequence of tests, including a first test and subsequent tests, can be run on a set of electrostimulation vectors. After the first test, the result of the first test can be immediately displayed using the user interface 145 while the subsequent tests proceed. The display can include an indication that tests are ongoing, and an indication that test result information can be displayed or updated in real-time as more test result information is acquired.

In an example, a user can interact with the progress of a sequence of tests in real-time. A user can pause and resume testing, such as by selecting appropriate buttons on the interactive user interface display 202 or 402. A user can elect to pause testing in response to a result presented in the Results region 470.

In an example, a user can enter text-based or graphical information corresponding to a particular test vector. In the illustrative example of FIG. 4, the note 495 ("Patient was lying horizontally during test") can be added to indicate that, while the pacing parameter tests corresponding to the first electrostimulation vector 465 were in progress, the patient was lying horizontally. Similarly, a general note "B" 491 was added to the result corresponding to test vector 261 and test result 462. Such a general note can be selected from a predefined list of commonly used notes, such as using a drop-down box.

A graphical representation of a vector, such as the pictorial arrow representing test vector 261, can be displayed in an identifiable color to indicate a vector associated with an unfavorable test result. For example, if phrenic nerve stimulation is detected during a test of vector 261, the representation of the test vector can be shown using a gray arrow symbol. The device-readable instructions for performing the instruction can be configured such that an unfavorable test result, such as phrenic nerve stimulation, associated with a particular vector will automatically pause testing or alert an attending user. In an example, tests to be performed after obtaining an unfavorable result can be re-ordered to prevent additional testing on a vector associated with an unfavorable result.

The Results region 470 can include multiple rows and columns. In the illustrative example of FIG. 4, the Results region 470 includes four columns: a first column 471 to describe the tested vector, wherein the tested vector can be presented using user-defined or system-defined electrode designators; a second column 472 to present the results of a pacing threshold test; a third column 473 to present the results of a phrenic nerve stimulation threshold test; and a fourth column 474 to present the results of an impedance measurement test. In an example, any number of columns can be presented in the Results region 470, and any or all of the columns can include descriptive headers 479.

The Results region 470 can include selectable rows or columns. Selection of a column can sort the test results in ascending or descending order according to the results in the selected column. Selection of a row can permit a user to re-order the presentation of the results, such as by dragging and dropping the selection using a mouse. Selection of a vector or set of vectors can indicate a vector or set of vectors for use in programming the ambulatory medical device 101. The Results region 470 can include a selected or highlighted portion 480. The selected or highlighted portion can be visually indicated such as by showing a box around the test results, or presenting the test information in a bold font, among other display techniques. A vector with the best results, such as determined according to an instruction routine executed by the processor circuit 143 or processor circuit 103, can be highlighted. The graphical representation of the vector associated with a result selected in the Results region 470 can be visually indicated, such as by using a different display color.

In the example of FIG. 4, the interactive user interface display 402 can include a set of buttons 250. The set of buttons 250 can include a button to program a selected pacing configuration, such as the "Program Selected LV Pacing Configuration" button 452. The "Program Selected LV Pacing Configuration" button 452 can be used in conjunction with a selection of a vector, from among the vectors presented in the Results region 470 or the graphical representation of electrostimulation electrodes 260, to program the ambulatory medical device 101.

The set of buttons 250 can include a button to indicate that additional pacing configurations will be tested. The "Continue Searching" button 451 can be used to resume testing if the test sequence has been paused or stopped. The "Continue Searching" button 451 can be used to return to a previous user interface display, such as the interactive user interface display 202, wherein a user can indicate combinations of electrostimulation electrodes or vectors for test. An indication of previously tested vectors, and the test results associated with the previously tested vectors, can also be displayed. In an example, the previously tested vectors can be displayed using the Results region 470.

Figure 5:
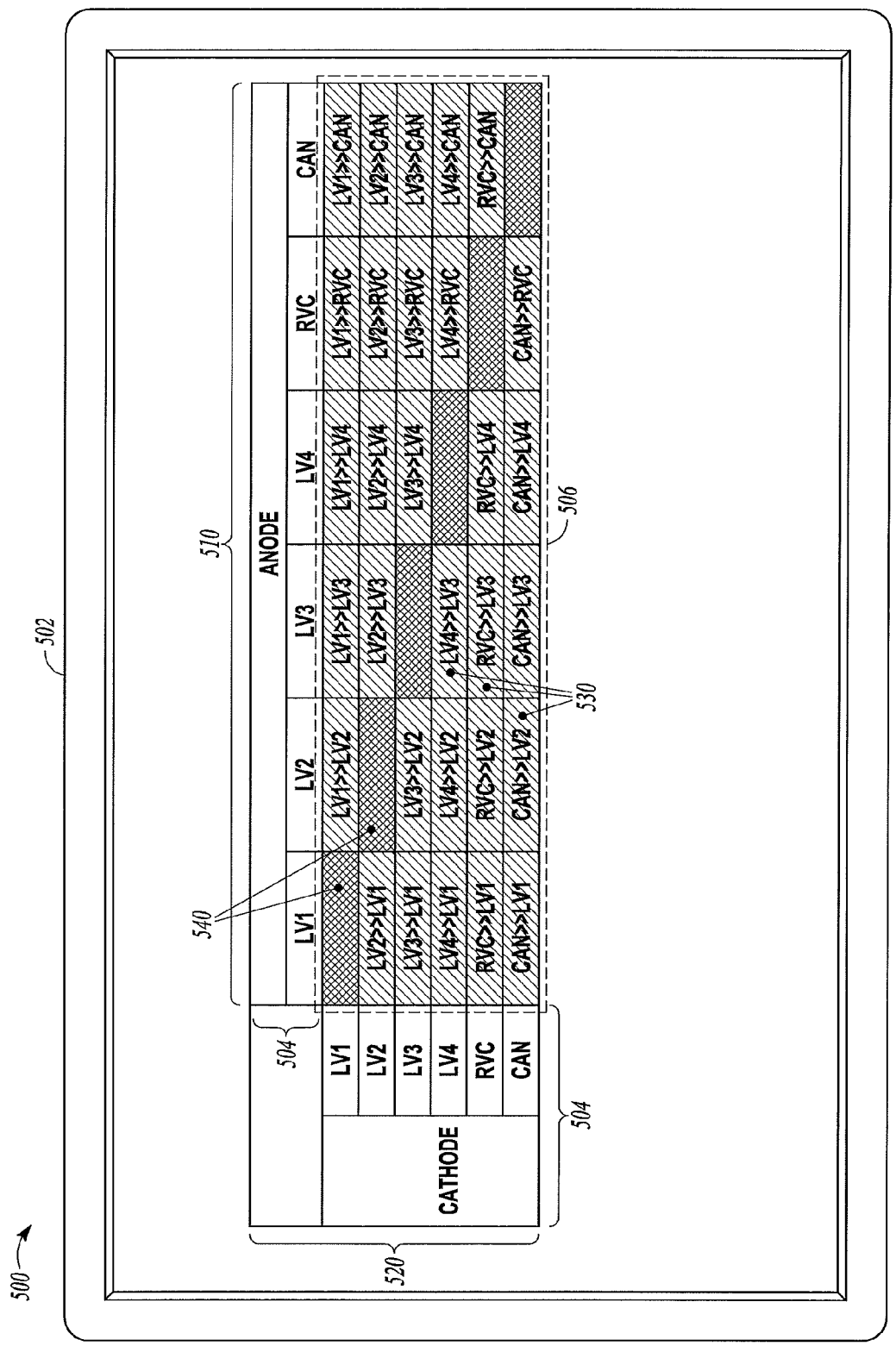
FIG. 5 illustrates generally an example of a portion of a system that can include a tabular interactive representation of electrodes.

FIG. 5 is a diagram illustrating generally an example of a user interface 500 comprising the interactive user interface display 502. The user interface 145 can be configured to present a tabular user interface to a user. The interactive user interface display 502 can include, among other features, a table wherein the rows and columns represent electrostimulation electrodes. The interactive user interface display 502 can present several table columns 510 wherein a particular column corresponds to an electro stimulation electrode that is available for use as an anode of an electrostimulation or sensing vector. The interactive user interface display 502 can present several table rows 520 wherein each row corresponds to an electrostimulation electrode that is available for use as a cathode of an electrostimulation or sensing vector. The individual rows and columns can be sortable and the order of the displayed rows and columns can be modified by a user. Entire rows or columns can be electively omitted from the display by a user.

In the illustrative example of FIG. 5, there can be six possible anodes (designated in the header cells 504 by LV1, LV2, LV3, LV4, RVC, and Can) and six possible cathodes (designated in the header cells 504 by LV1, LV2, LV3, LV4, RVC, and Can) presented, each anode and cathode represented by an available electrostimulation electrode. Additional anodes and cathodes can be readily formed by combining any of the available electrostimulation electrodes to define a multipolar pacing vector, such as described above in the discussion of FIG. 3A, or below in the discussion of FIG. 6A. The designations used in the header cells 504, such as the designators "LV1," "LV2," etc., in FIG. 5, can be user-defined such that many individual electrodes can be meaningfully represented to the user. In an example, the designation information 271 can be used to populate the header cells 504.

Possible combinations of electrostimulation electrodes can be represented by the data cells 506 that populate the table. In the illustrative example of FIG. 5, the data cells 506 comprise thirty-six individual cells. In an example, six of the thirty-six data cells can be rendered opaque and without visible content. The six opaque cells 540 can designate invalid electrostimulation electrode combinations, or invalid vectors. For example, an electrostimulation vector cannot be formed with only one electrode. The opaque cells in the tabular, interactive user interface display 502 represent single-electrode vectors, or invalid vectors. The remaining valid vectors or valid electrostimulation electrode combinations, such as those represented by the light gray cells 530, can be made available to a user for selection. Selection of any of the six opaque cells 540 can be automatically precluded.

The data cells 506 comprising valid vectors can include text information describing the vector. For example, the electrode combination of LV1 at the anode and LV2 at the cathode corresponds to a data cell that includes the text "LV2>>LV1." The text "LV2>>LV1" in the data cell can represent the available electrostimulation vector formed between anode LV1 and cathode LV2.

Figure 6A:
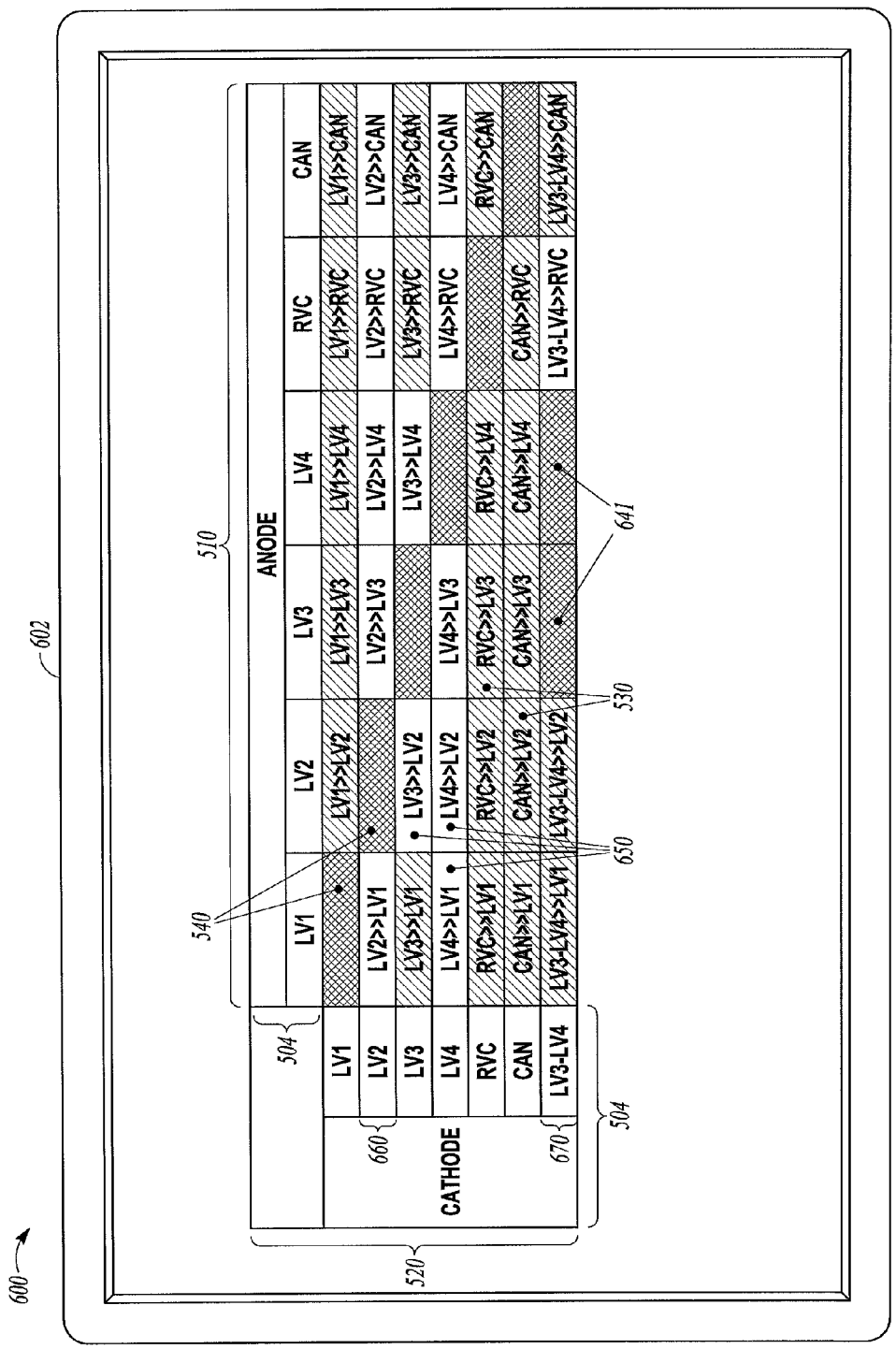
FIG. 6A illustrates generally an example of a portion of a system that can include a tabular interactive representation of a selection of multiple electrostimulation electrode combinations or vectors.

FIG. 6A is a diagram illustrating generally an example of a user interface 600 comprising the interactive user interface display 602. The user interface 145 can be configured to present a tabular interactive interface to a user. A display can present six possible anodes (designated in the header cells 504 by LV1, LV2, LV3, LV4, RVC, and Can) and seven possible cathodes (designated in the header cells 504 by LV1, LV2, LV3, LV4, RVC, Can, and LV3-LV4), each anode and cathode represented by an available electrostimulation electrode. A multipolar electrode can be included as an available cathode. A user can electively combine any two or more of the available cathodes or anodes to form a multi-polar electrode. A user can manually indicate the addition of a multipolar electrode such as by using selectable table elements or configuration buttons to indicate the selection of a multipolar electrode. A row 670 indicating the multipolar LV3-LV4 cathode can be added to the interactive user interface display 602. The invalid vectors 641 associated with the multipolar electrode can be presented using opaque cells.

Figure 6B:
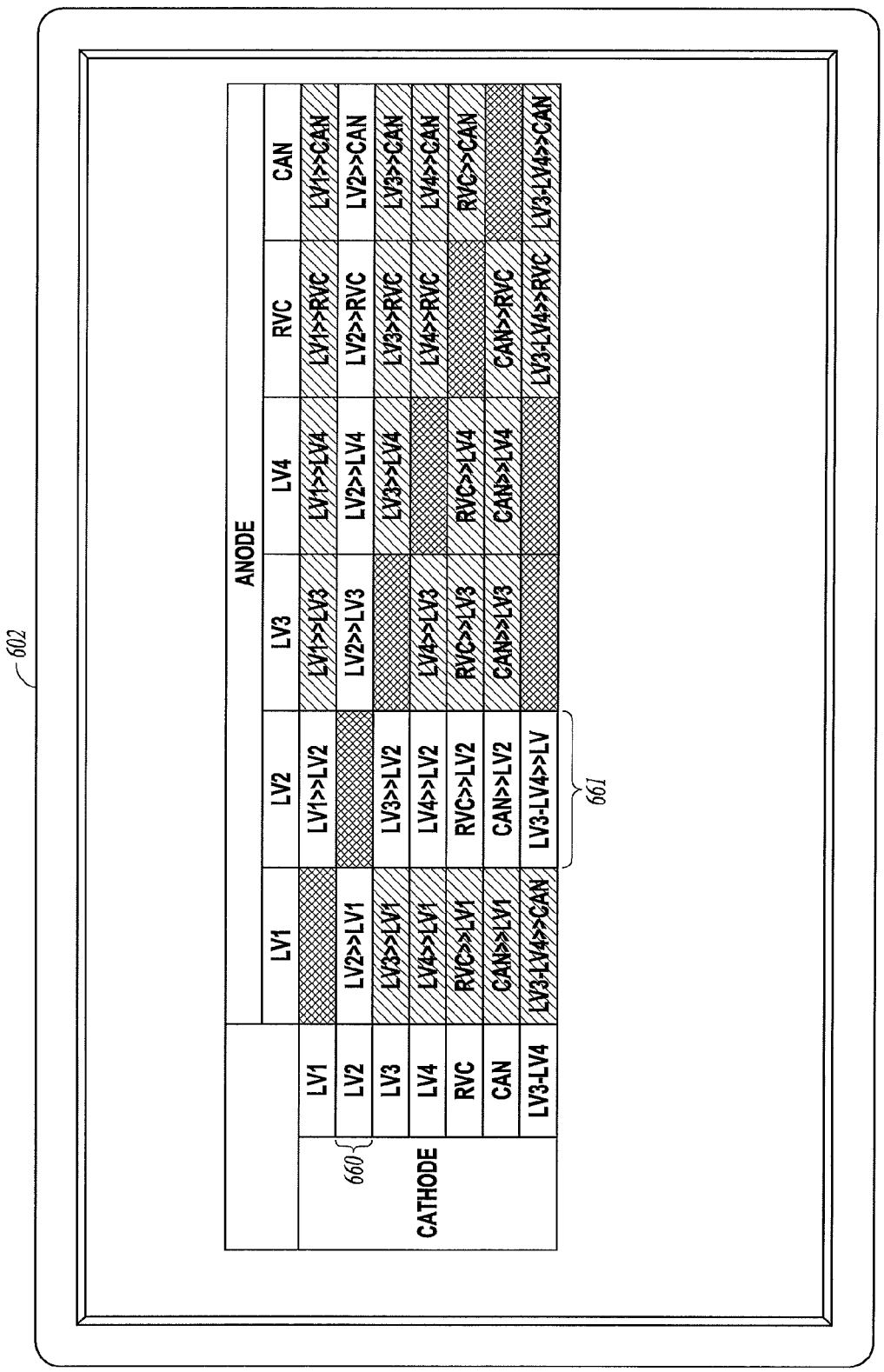
FIG. 6B illustrates generally an example of a portion of a system that can include a tabular interactive representation of a selection of multiple electrostimulation electrode combinations or vectors, including an interactive representation of a combination of electrostimulation electrodes.

The interactive user interface display 602 can indicate a selection of vectors for test, such as using color coding. Cells without background shading 650 can indicate a selected electrostimulation electrode combination or vector. Selected cells, rows, or columns can be highlighted, bolded, color-coded, or otherwise visually distinguishable from unselected cells, rows, or columns. In an example, all vectors associated with a particular anode or cathode can be selected, such as by selecting a header cell 504 corresponding to the desired cathode or anode. All vectors of a predefined category can be selected, such as by using the Select Vector Category region 280. In the example of FIG. 6A, the row 660 corresponding to the LV2 cathode has been selected, and five electrode combinations or vectors can be designated for a test sequence. In the example of FIG. 6B, selecting LV2 can indicate a selection of all electrode combinations or vectors associated with electrode LV2. The vectors represented in the row 660 corresponding to the LV2 cathode and the column 661 corresponding to the LV2 anode can be designated for test. The representations of the electrode combinations associated with LV2 can be highlighted, such as displayed in cells without background shading 650.

In an example, a user can choose to omit certain electrostimulation electrodes from test, such as by selecting an individual table cell or by designating an entire row or column for omission. An "Omit Electrode" button can be included, such as using the interactive user interface display 602, to facilitate manually removing electrostimulation electrodes from the set of available electrostimulation electrodes or electrostimulation electrode combinations.

In an example, the order of selection can determine the test sequence. The test sequence can be assignable subsequent to the selection of electrode combinations or vectors. A test sequence can be indicated such as by using the Selected Vectors region 240 to order a list of selected vectors.

Figure 7:
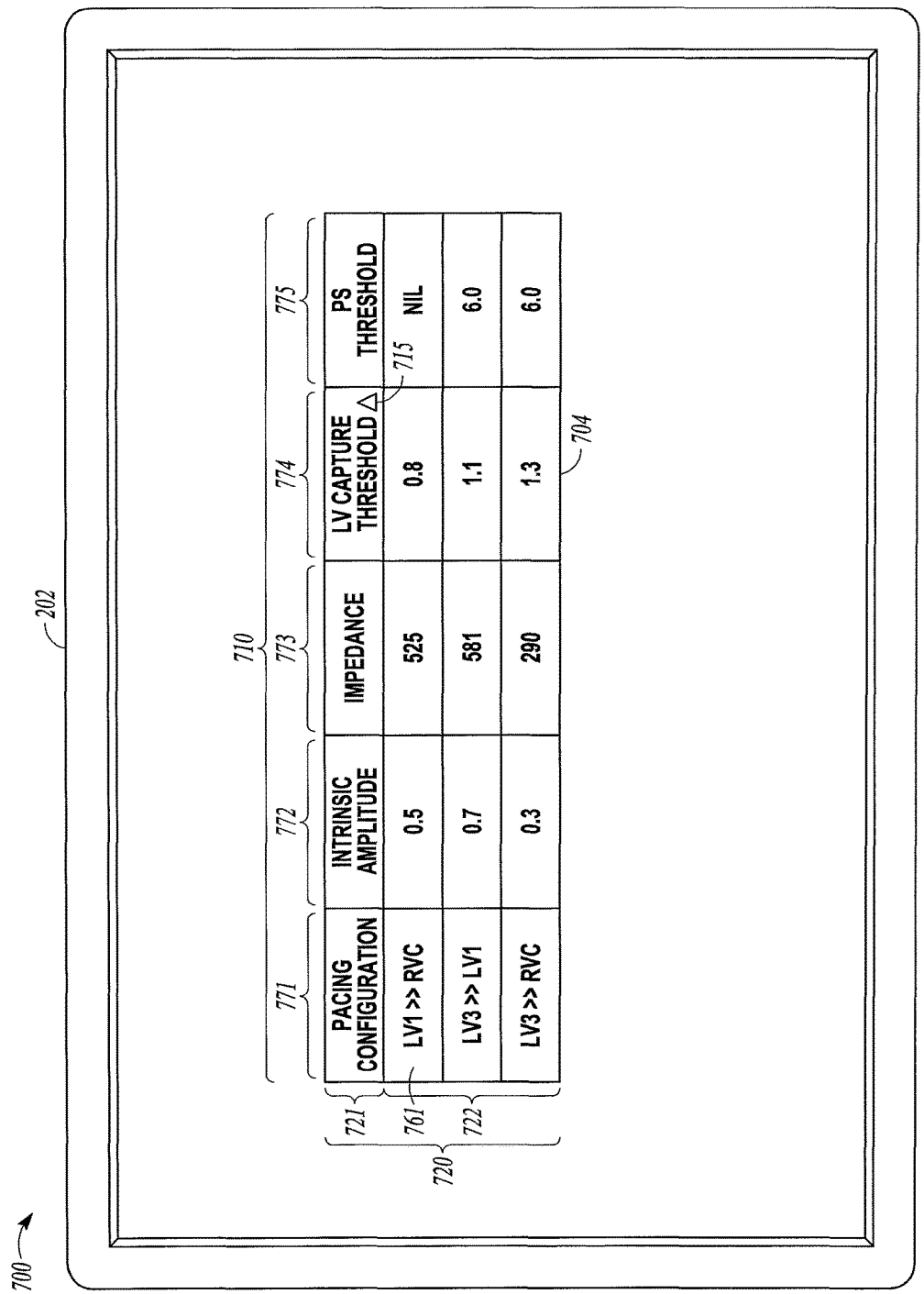
FIG. 7 illustrates generally an example of a portion of a system that can include a tabular interactive representation of an indication of results of an electrostimulation parameter test.

FIG. 7 is a diagram illustrating generally an example of a text-based user interface 700 comprising an interactive user interface display 202. The user interface 145 can be configured to present the interactive user interface display 202 to a user. The interactive user interface display 202 can include, among other features, a results table 704. The results table 704 can include several columns 710 and rows 720. The results table 704 can include a header row 721 and several data rows 722.

The results of a set of pacing parameter tests can be displayed in the results table 704 on the interactive user interface display 202. The results corresponding to a first electrostimulation vector 761 can be displayed in the results table 704, such as in a first row. Notes can be added to the results table 704 such as using user interface 145 to enter text in a cell, or to enter text in an area associated with a particular cell.

The results table 704 can include multiple rows and columns. In the illustrative example of FIG. 7, the results table 704 can comprise five columns: a first column 771 to describe the tested vector, wherein the tested vector can be presented using user-defined or system-defined electrode designators; a second column 772 to present the results of an intrinsic amplitude test; a third column 773 to present the results of an impedance measurement test; a fourth column 774 to present the results of a left ventricular capture threshold test; and a fifth column 775 to present the results of a phrenic nerve stimulation threshold test. Any number of columns can be presented in the results table 704, and any or all of the columns can include descriptive headers, such as in header row 721.

The results table 704 can include selectable rows or columns. A selection of a column can sort the test results in ascending or descending order according to the results in the selected column. A visual indication, such as an icon 715, can indicate that the data has been sorted according to the results presented in a particular column or set of columns. Selection of a row can permit a user to re-order the presentation of the results. Selection of a vector or set of vectors can indicate a vector or set of vectors for use in programming the ambulatory medical device 101.

In an example, any aspect of a graphical user interface, such as the graphical interactive user interface display 502, can be combined with any aspect of a text or table-based user interface, such as the interactive user interface display 602. Similarly, any aspects of a text-based user interface can be combined with any aspects of a graphical user interface to create a robust and interactive user experience that can simultaneously present and update graphical and textual information.

Figure 8:
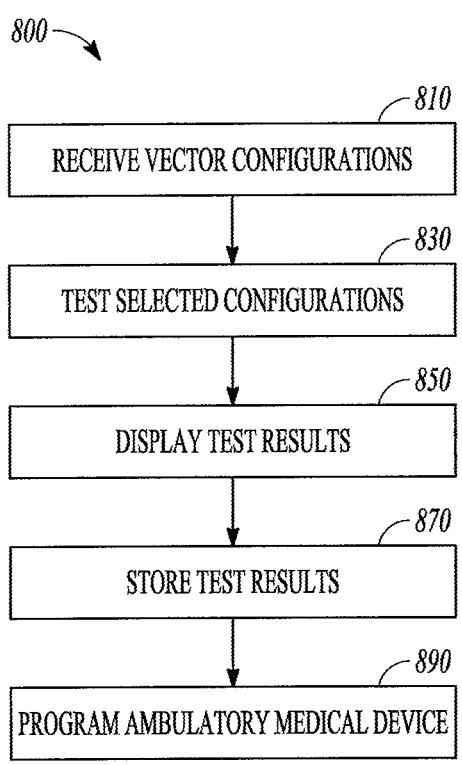
FIG. 8 illustrates generally an example that can include receiving vector configurations, testing selected configurations, displaying test results, storing test results, or programming an ambulatory medical device.

FIG. 8 illustrates generally an example 800 that can include receiving vector configurations 810, testing received vector configurations 830, displaying test results 850, storing test results 870, and programming an ambulatory medical device 890.

At 810, a vector configuration can be received. This can include one or more of receiving a pacing configuration or a sensing configuration. A pacing configuration can include one or more electrostimulation electrodes configured for delivering or sensing an electrical signal. A vector configuration can be received from an interactive user interface display, such as an interactive user interface display 202 configured to display graphics and text. A vector configuration can be received from a system-generated combination of one or more electrostimulation electrodes. Receiving a vector configuration can include receiving a vector configuration from a user of a device incorporating a user interface 145. Receiving vector configurations can involve one or more sequences of operational steps involving selections of electrostimulation electrode combinations or vectors, such as described above in the discussion of FIG. 3A. Receiving vector configurations can include adding one or more vector configurations to a set of configurations, or removing one or more vector configurations from a set of configurations. Receiving vector configurations can include receiving an indication of one or more vector configurations for test, or can include receiving an exemption of one or more vector configurations from test. Receiving vector configurations can include receiving a test sequence, or receiving a selection of tests to be performed on the received vector configurations.

At 830, selected vector configurations can be tested. The testing can be initiated at the user interface 145. The testing can be directed by the processor circuit 143 of the external assembly 140. The testing can be performed by the processor circuit 103 in an implantable medical device. Testing the selected configurations can include performing a sequence of tests on one or more electrostimulation electrode combinations or vectors. The testing can include performing a first test on all vectors according to a first sequence. The testing can include performing a second test on all vectors according to a second sequence, the second sequence different than the first sequence. The testing can include performing a first sequence of tests on a first vector. The testing can include performing a second sequence of tests on a second vector, the second sequence differing from the first sequence. A first set of vectors can undergo a first set of tests, and a second set of vectors can undergo a second set of tests. The first and second sets of vectors can differ. The first and second sets of tests can differ.

At 850, the results of the tests performed at 830 can be displayed. The results can be displayed on a user interface 145, such as using the interactive user interface display 202. Displaying the results can include calculating a comparison metric, such as a pacing configuration score, such as using Equation 1:

$$PS_{presence} * \left( \begin{array}{c} (Weight_1 * CaptureThreshold) + \\ (Weight_2 * IntAmp) + (Weight_3 * Z) \end{array} \right) = PacConfigScore \quad \text{Equation 1}$$

wherein $PS_{presence}$ is a boolean equal to 0 if phrenic nerve stimulation is present and equal to 1 if phrenic nerve stimulation is absent, CaptureThreshold is a numerical value associated with a cardiac capture threshold measurement, IntAmp is a numerical value associated with an intrinsic amplitude measurement, Z is a numerical value associated with an impedance measurement, and $Weight_X$ is the priority-based weight given to each parameter. A calculated pacing configuration score can be used such as to determine a test result display order. For example, a configuration with the highest pacing configuration score can be presented in the first row in a table of results, such as at first row 475 in Results region 470. The pacing configuration score can be incorporated into a graphical or text-based user interface display, such as at the test result display location 466. The pacing configuration score can be used by a clinician to quickly rank the relative performance of multiple electrode combinations or vectors. In an example, several pacing configuration scores can be calculated. In an example, a user can define the one or more equations used to compute a pacing configuration score. In an example, a configuration score can be calculated for a sensing vector.

At 870, the results of the tests performed at 830 can be stored. The results can be stored in the memory circuit 104 in the ambulatory medical device 101 or in the memory circuit 144 in the external assembly 140. The results can be transmitted to an external device for further processing or archiving. Stored test results can be retrieved by the ambulatory medical device 101 or the external assembly 140 and used to determine a change in therapy.

At 890, the ambulatory medical device 101 can be programmed. In an example, an implantable medical device can be programmed by receiving a vector configuration. A vector configuration can be selected, such as from a list presented in the Results region 470, and the selected configuration can be transmitted to the ambulatory medical device 101 such as after selecting a button 452. The ambulatory medical device 101 can be programmed to use a first combination of implantable leads comprising multiple electrodes. The ambulatory medical device 101 can be programmed to use a plurality of electrostimulation electrodes to deliver multiple therapies or sense cardiac parameters at multiple sites.

Figure 9:
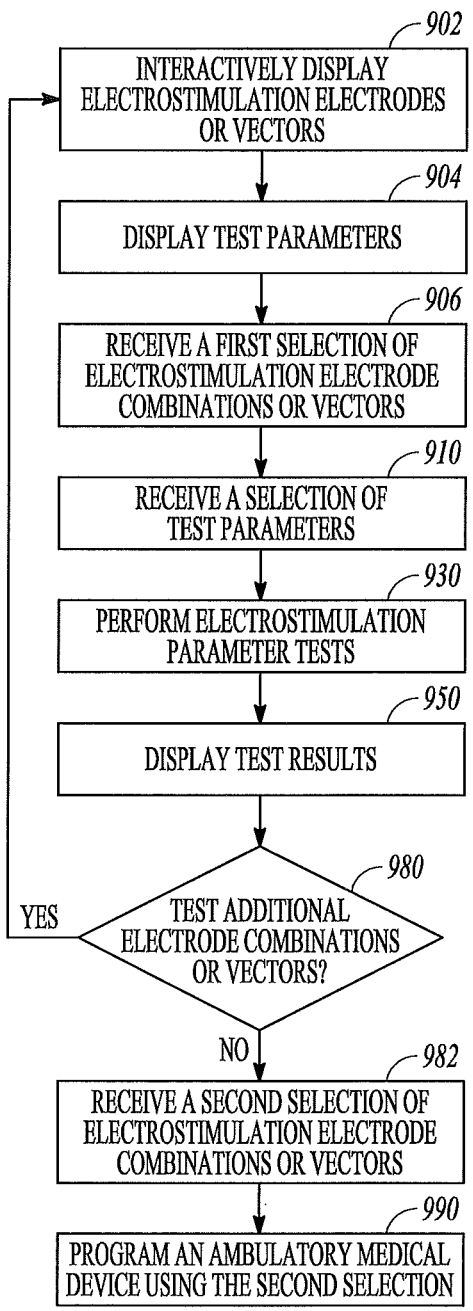
FIG. 9 illustrates generally an example that can include interactively displaying electrostimulation electrodes or vectors, displaying test parameters, receiving a first selection of electrostimulation electrode combinations or vectors, receiving a selection of test parameters, performing electrostimulation parameter tests, displaying test results, deciding whether or not to test additional electrode combinations or vectors, receiving a second selection of electrostimulation electrode combinations or vectors, or programming an ambulatory medical device using the second selection.

FIG. 9 illustrates generally an example 900 that can include interactively displaying electrostimulation electrodes or vectors 902, displaying test parameters 904, receiving a first selection of electrostimulation electrode combinations or vectors 906, receiving a selection of test parameters 910, performing electrostimulation parameter tests 930, displaying electrostimulation parameter test results 950, deciding whether or not to test additional electrode combinations or vectors 980, receiving a second selection of electrostimulation electrode combinations or vectors 982, and programming an ambulatory medical device using the second selection 990.

At 902, a set of electrostimulation electrodes or vectors can be interactively displayed. The set can be graphically displayed using the interactive user interface display 202 and the interactive representation of electrostimulation electrodes 260. A graphical representation of implantable or external leads can be shown on a display screen. The graphical representation of implantable or external leads can include a graphical representation of individual electrodes, or combinations of electrodes on the implantable or external leads. The graphical representation of individual electrodes, or combinations of electrodes, can include a text-based representation of electrodes, such as can be displayed using the interactive user interface display 502. The interactive user interface display 502 can be configured to display, among other features, a table wherein the rows and columns represent electrostimulation electrodes.

The interactive display elements representative of electrodes can include selectable icons presented using a computer screen. Interactive display elements representative of pacing or sensing vectors can be selectable icons presented using the user interface 145. The vectors can be illustrated using a dotted line and an arrowhead. The vectors can be illustrated using a graphic representative of an electric field, such as a series of arced field lines. Electrostimulation electrode combinations or vectors currently available for test can be displayed.

At 904, a set of test parameters can be displayed. The set of test parameters can be displayed graphically or in a text-based list format. The interactive user interface display 202 can be configured to display the set of test parameters. The set of test parameters can be displayed in response to a user selection, or can be configured to display in a new display window or region using the user interface 145.

At 906, a first selection of electrostimulation electrode combinations or vectors can be received. The first selection can be received from a user. The first selection can be received in response to the interactive display of electrostimulation electrodes or vectors at 902. The receiving can occur at the user interface 145, such as using a touch screen display. The interactive user interface display 202 can be configured to receive a selection of a plurality of electrostimulation electrodes vectors. The received selection of electrostimulation electrode combinations or vectors can be stored in the memory circuit 104 or the memory circuit 144. The received selection of electrostimulation electrode combinations or vectors can define a test sequence, the sequence sortable by a user or by a system-defined priority schedule. The received selection of electrostimulation electrode combinations or vectors can be used to highlight a region of a graphical display, such as by highlighting a region of the display, color-coding a selected region of the display, or otherwise obviating an area of a display.

At 910, a selection of test parameters can be received. The selection of test parameters can be received from a user. The selection of test parameters can be received in response to the display of test parameters at 904. The receiving can occur at a user interface 145, such as using an LCD computer monitor and input devices such as a mouse and keyboard. The interactive user interface display 202 can be configured to receive a selection of a plurality of test parameters. The received selection of test parameters can be stored in the memory circuit 104 or the memory circuit 144, or in an external device. The received selection of test parameters can define a test sequence, the sequence sortable by a user or by a predefined priority schedule.

At 930, electrostimulation parameter tests can be performed. The performed tests can include an intrinsic amplitude measurement, an impedance measurement, or a left ventricular capture voltage measurement, among others. The tests can be performed according to a predefined sequence. The tests can be performed in a sequence determined by a user, the sequence entered using the external assembly 140. One or more results can be associated with the performance of each test. The results can include a computation of a comparison metric. A comparison metric can include a metric calculated using a test result of the electrostimulation parameter test. A comparison metric can be used by a processor-driven device, such as the ambulatory medical device 101, to automatically select a pacing configuration. The comparison metric can be used to determine a display sequence for the results.

At 950, the results of the electrostimulation parameter tests can be displayed. The results can be displayed via the user interface 145, such as using an interactive user interface 402 and a Results region 470. A comparison metric can be displayed alongside the display of the results. Displaying the results can include displaying a graphical or text-based result in visual correspondence with the graphical representation of the vector, such as in close proximity to the representation of the vector. The results of a pacing threshold test and a phrenic nerve stimulation threshold test can be displayed in visual correspondence with a graphical representation of a vector, such as in the illustrative example of the interactive user interface 402 at 466. Graphically displaying the test results at 950 can include displaying a Results region 470 that can include a list of tested vectors and the results associated with each vector. The graphical display of the test results can include differentiating the results using different fonts, colors, animations, or display areas, among others. Receiving an unexpected or unfavorable result at 950 can halt testing altogether.

At 980, a decision can be made whether or not to test additional electrode combinations or vectors. A calculated comparison metric can be analyzed to assess whether or not any of the tested vectors meet or exceed a predetermined threshold level of the comparison metric. In an example, the comparison metric can be raw data, such as a numerical value representing a measured impedance level. If the comparison metric exceeds a threshold value, no additional tests are required and the system can proceed to the next step. In an example, only a small number of electrostimulation electrode combinations may have been tested and a user can elect to test additional combinations. If additional tests are desired, the user can be redirected to the first interactive display of electro stimulation electrodes or vectors at 902. The previously tested vectors can be indicated to the user upon redirection to the first interactive display. If additional tests are not desired, the user can proceed to 982.

In an example, the steps 930, 950, or 980, among others, can be performed concurrently. A test procedure started at 930 can include displaying test results at 950 while additional tests are performed contemporaneously with the displaying at 950. A user can elect to pause or stop a test at 980 to consider whether or not to test additional electrode combinations or vectors. The decision of whether or not to test additional electrode combinations or vectors can be made while a previous set of parameter tests is ongoing. A user can receive the test results displayed at 950, and adjust testing parameters in real-time for subsequent tests. In an example, a user can receive an unfavorable test result at 950, and can choose to remove from the queue of pending tests all test configurations involving the vector associated with the unfavorable result.

At 982, a second selection of an electrostimulation electrode combination or vector can be received. In an example, the selection can be received from among the displayed test results at 950, such as can be displayed in the Results region 470. The selection can be received from a user interface 145. The selection can be automatically received using the comparison metric.

At 990, an ambulatory medical device can be programmed using the second selection. The programming can occur subsequent to the selection of a button, such as the "Program Selected LV Pacing Configuration" button 452. The election to program the ambulatory medical device 101 can occur via the user interface 145. The configuration to be programmed can reside in the memory circuit 144, and can be transmitted wirelessly via the communication circuit 142 in the external assembly 140 to the communication circuit 102 in the ambulatory medical device 101. The ambulatory medical device 101 can be configured to use a pacing configuration in response to receiving information about the second selection. The ambulatory medical device 101 can be programmed automatically by the external assembly 140 such as by selecting an optimal vector configuration using the processor circuit 143 to analyze received test results and comparison metrics associated with the test result. The processor circuit 143 can perform additional vector selection algorithms to aid in selecting an optimal vector configuration. The external assembly 140 can recommend vector configurations to a user, such as via the user interface 145. A user can determine whether or not to apply new vector configuration parameters to the ambulatory medical device 101.

Additional Notes

The electrostimulation electrodes referenced throughout this specification can be used for either delivery or sensing of electrical signals. Such delivery or sensing of an electrical signal can occur via an "electrostimulation electrode combination," or "electrode combination," such as can define an "electrostimulation vector," or "vector." An electrostimulation vector, or vector, can be a configuration involving two or more electrodes for the delivery or reception of an electrical signal.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method comprising:
   providing to a user an interactive representation of a first set of electrostimulation electrodes, the interactive representation including a graphical representation of one or more cardiac electrostimulation leads and positions of the electrostimulation electrodes thereon;
   receiving a first selection of an electrostimulation electrode;
   providing a visual indication of the first selection using the interactive representation; and
   interactively using the first selection, wherein interactively using the first selection comprises performing at least:
   displaying, using the interactive representation, device-measured results of an impedance measurement test for an electrostimulation electrode combination or a vector associated with the first selection; and
   indicating, using the interactive representation, the first selection by superimposing the first selection over an image of a heart.

2. The method of claim 1, wherein interactively using the first selection comprises providing a second set of electrostimulation electrodes that is available for use with the first selection.

3. The method of claim 2, comprising receiving from the user a second selection of an electrostimulation electrode or vector, selected from among the second set of electrostimulation electrodes or vectors, the second selection performed by the user using the interactive representation.

4. The method of claim 1, wherein the interactively using the first selection comprises at least one of:
providing, in visual correspondence with the first selection, a second set of electrostimulation electrodes or vectors that is available for use with the first selection; or
displaying information indicative of a parameter test result in visual correspondence with the electrode combination or vector associated with the result.

5. The method of claim 1, wherein the providing to a user an interactive representation of a first set of electrostimulation electrodes includes displaying a pictorial interactive representation of a set of electrostimulation electrodes or vectors, including a user-selectable representation of an electrostimulation electrode or vector.

6. The method of claim 1, wherein the providing to a user an interactive representation of a first set of electrostimulation electrodes includes displaying a tabular interactive representation of a set of electrostimulation electrodes or vectors, including a user-selectable table element representative of an electrostimulation electrode or vector.

7. The method of claim 1, wherein the receiving a first selection of an electrostimulation electrode includes receiving the first selection from a user using the interactive representation.

8. The method of claim 1, comprising:
providing to a user an interactive representation of a set of one or more parameter tests or parameter test characteristics; and
performing interactive user-controllable parameter testing using a selection of a parameter test or parameter test characteristic received from the user.

9. The method of claim 8, wherein the performing interactive user-controllable parameter testing includes adjusting subsequent parameter tests in response to a received parameter test result.

10. The method of claim 8, comprising:
calculating a comparison metric using the test result of the parameter test; and
using the comparison metric, performing at least one of:
displaying the comparison metric;
analyzing the comparison metric;
programming an ambulatory medical device; or
organizing the displayed information indicative of a parameter test result.

11. The method of claim 1, wherein the receiving the first selection of an electrostimulation electrode includes receiving a selection of an electrostimulation electrode configured for intravascular delivery of electrostimulation energy to multiple locations at or near a left ventricle of a heart.

12. An apparatus, comprising:
a display configured to provide an interactive representation of a set of electrostimulation electrodes or vectors, wherein the interactive representation comprises:
a graphical representation of one or more cardiac electrostimulation leads and positions of the electrostimulation electrodes thereon;
a first input, including an interactive visual indication indicating a first selection of an electrostimulation electrode or vector; and at least:
an interface configured to receive a selection of one or more tests to perform on the first selection of an electrostimulation electrode or vector; and
an interactive visual indication, displayed using the interactive representation, of a device-measured result of an impedance measurement test for an electrostimulation electrode combination or vector associated with the first selection; and
wherein the interactive representation is further configured to display the first selection of an electrostimulation electrode or vector superimposed over the image of a heart.

13. The apparatus of claim 12, wherein the interactive representation comprises an interactive visual indication, provided using the interactive representation, of a second set of electrostimulation electrodes or vectors that is available for use with the first selection.

14. The apparatus of claim 12, wherein the interactive representation comprises an interactive visual indication, displayed using the interactive representation, of information indicative of a parameter test result for an electrostimulation electrode combination or vector associated with the first selection.

15. The apparatus of claim 12, wherein the interactive representation comprises an interactive user-control, configured to perform, using the interactive representation, interactive user-controllable parameter testing using the first selection.

16. The apparatus of claim 12, wherein the interactive representation comprises an interactive visual indication of a second set of electrostimulation electrodes or vectors that is available for use with the first selection, the second set provided using the interactive representation and in visual correspondence with the first selection.

17. A method comprising:
providing to a user an interactive representation of a first set of cardiac electrostimulation electrodes;
receiving a first selection of a cardiac electrostimulation electrode or electrostimulation vector;
providing a visual indication of the first selection using the interactive representation, wherein providing the visual indication of the first selection includes a color change representative of the selection of the cardiac electrostimulation electrode or electrostimulation vector;
receiving from a user a selection of one or more tests to perform on the first selection of an electrostimulation electrode;
interactively using the first selection including displaying device-measured results of an impedance measurement test for a cardiac electrostimulation electrode combination or an electrostimulation vector associated with the first selection; and
displaying, using the interactive representation, the first selection of the cardiac electrostimulation electrode or electrostimulation vector superimposed over an image of a heart.

18. The apparatus of claim 17, wherein the image of the heart is configured to be rotated in virtual three dimensional space.

* * * * *